(12) United States Patent
Feinberg et al.

(10) Patent No.: US 8,835,169 B2
(45) Date of Patent: Sep. 16, 2014

(54) COMPOSITIONS, METHODS AND SYSTEMS FOR PREPARATION OF A STEM CELL-ENRICHED CELL POPULATION

(75) Inventors: Stephen E. Feinberg, Ann Arbor, MI (US); Kenji Izumi, Ann Arbor, MI (US); Cynthia L. Marcelo, Ann Arbor, MI (US); Yasushi Fujimori, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 966 days.

(21) Appl. No.: 11/257,274

(22) Filed: Oct. 24, 2005

(65) Prior Publication Data

US 2006/0148075 A1     Jul. 6, 2006

Related U.S. Application Data

(60) Provisional application No. 60/621,262, filed on Oct. 22, 2004.

(51) Int. Cl.
    *C12N 5/071*      (2010.01)

(52) U.S. Cl.
    CPC .......... *C12N 5/0629* (2013.01); *C12N 2500/99* (2013.01); *C12N 5/063* (2013.01)
    USPC .......................................... 435/366; 435/325

(58) Field of Classification Search
None
See application file for complete search history.

(56) References Cited

U.S. PATENT DOCUMENTS

| | | | | |
|---|---|---|---|---|
| 5,093,234 | A * | 3/1992 | Schwartz | 435/7.21 |
| 6,506,600 | B2 * | 1/2003 | Hermonat et al. | 435/371 |
| 2002/0042133 | A1 * | 4/2002 | Baur | 435/455 |
| 2005/0186286 | A1 * | 8/2005 | Takami | 424/572 |
| 2006/0147426 | A1 * | 7/2006 | Schiller et al. | 424/93.7 |

FOREIGN PATENT DOCUMENTS

WO     WO-0172970 A2     10/2001

OTHER PUBLICATIONS

Izumi K, Takacs G, Terashi H, Feinberg SE. Ex vivo development of a composite human oral mucosal equivalent. J Oral Maxillofac Surg. May 1999;57(5):571-7.*
Rivier M, Safonova I, Lebrun P, Griffiths CE, Ailhaud G, Michel S. Differential expression of peroxisome proliferator-activated receptor subtypes during the differentiation of human keratinocytes. J Invest Dermatol. Dec. 1998;111(6):1116-21.*
Flow Cytometry Size Calibration Kit Product Information. Molecular Probes, Apr. 4, 2003, pp. 1-2 (<http://probes.invitrogen.com/media/pis/mp13838.pdf>).*
Fisher Scientific Biotechnology Catalog, 1995.pp. 1,238-246.*
Izumi K, Terashi H, Marcelo CL, Feinberg SE.Development and characterization of a tissue-engineered human oral mucosa equivalent produced in a serum-free culture system. J Dent Res. Mar. 2000;79(3):798-805.*
Izumi et al in "Intraoral grafting of an ex vivo produced oral mucosa equivalent: a preliminary report" (Int. J. Oral Maxillofac. Surg. 2003; vol. 32 pp. 188-197.*
Li et al in "Separation culture and identification of human epidermal stem cell in vitro" (Chinese Journal of Clinical Rehabilitation: vol. 7, No. 11, May 2003: pp. 1620-1621: Abstract only, hereafter "Li et al(2003)").*
Izumi et al 2004; "Development of a tissue engineered humanoral mucosa: from the bench to the bed side". Cells Tissues Organs 176,134-152).*
PCT International Search Report for PCT/US05/38199; 2 pages.
Barrandon et al., "Cell Size as a Determinant of the Clone-Forming Ability of Human Keratinocytes"; Proc. Natl. Adad. Sci., USA, vol. 82, pp. 5390-5394, Aug. 1985.
Janes et al., "Epidermal Stem Cells"; Journal of Pathology, 2002; 197:479-491; published online May 20, 2002 in Wiley InterScience (www.interscience.wiley.com).
Bata-Csorgo et al., "Kinetics and Regulation of Human Keratinocyte Stem Cell Growth in Short-Term Primary Ex Vivo Culture"; J. Clin. Invest., vol. 95, Jan. 1995, 317-327.
Mao-Qiang et al., "Peroxisome-Proliferator-Activated Receptor (PPAR)-γ Activation Stimulates Keratinocyte Differentiation"; J. Invest. Dermatol., Aug. 2, 2004, 123:305-312.
Supplementary European Search Report from EP 05817244 dated Apr. 29, 2009 (11 pages).
Dunnwald M et al: "Isolating a pure population of epidermal stem cells for use in tissue engineering" Experimental Dermatology, Blackwell Munsgaard, Copenhagen; DK, vol. 10, No. 1, Feb. 1, 2001, pp. 45-54, XP002182788 ISSN.
Romano Andre C et al: "Different cell sizes in human limbal and central corneal basal epithelia measured by confocal microscopy and flow cytometry." IOVS, vol. 44, No. 12, Dec. 2003, pp. 5125-5129, XP002525977.
Li Amy et al: "Extensive tissue-regenerative capacity of neonatal human keratinocyte stem cells and their progeny." Journal of Clinical Investigation, vol. 113, No. 3, Feb. 2004, pp. 390-400, XP002525978 ISSN.
Izumi K et al: "Isolation of human oral keratinocyte progenitor/stem cells" Journal of Dental Research, vol. 86, No. 4, Apr. 2007, pp. 341-346, XP002525979 ISSN.

* cited by examiner

*Primary Examiner* — Catherine Hibbert
(74) *Attorney, Agent, or Firm* — Harness, Dickey & Pierce, P.L.C.

(57) ABSTRACT

In accordance with some preferred embodiments, without limitation, the present invention comprises compositions, methods and systems for preparation of stem-cell enriched cell populations from sources of biological materials by sorting cell types in relation to size.

11 Claims, 16 Drawing Sheets

COMPOSITIONS, METHODS AND SYSTEMS FOR PREPARATION OF A STEM CELL-ENRICHED CELL POPULATION

CROSS-REFERENCE TO RELATED APPLICATION

This application claims priority based on U.S. Provisional Patent Application No. 60/621,262, filed Oct. 22, 2004, which is hereby incorporated by reference in full.

GRANT INFORMATION

Work underlying the invention was supported in part by NIH Grant R01 DE13417. The government may have certain rights in the invention.

BACKGROUND

Stem cells have significant therapeutic implications and importance in the treatment of disease and pathological conditions in humans and other animals. Development of stem cell lines that produce or regenerate tissues of the human body has the potential to radically improve the quality and length of life. As an example, stem cells present opportunities to overcome tissue rejection by a patient's immune system. Stem cells might also be modified through genetic changes or other techniques to overcome immune rejection and/or to act as a vehicle for in situ delivery of other therapeutic agents.

In certain clinical therapies, contact with foreign or undefined proteins should be avoided in order to enhance stem cell use in ex vivo preparation of cells, genes and tissue therapies. In addition, isolation of a progenitor/stem cell enriched population would enhance predictability of fabrication and long-term graft success of tissue engineered constructs.

Tissue engineering and regenerative medicine has created considerable interest in the clinical application of stem cells to both regenerate body tissues and to deliver genetic material. As only one example among others, the production of a specific gene-transduced oral mucosal graft that can be used for reconstruction of major oral defects would be an asset to reconstructive surgery and/or gene therapy. The graft would then act both as a material for reconstruction and as a repository for in situ transmucosal delivery of recombinant growth factors or cytokines. Primary human keratinocytes fulfill most requirements for use in these treatment modalities. Compared with other types of human cells, keratinocytes can grow to generate cohesive sheets of epithelium for grafting onto patients. In addition, the transplanted grafts are readily visible over time allowing constant control and follow up as well as the local modulation of transgene expression using an appropriate promoter (Serrano et al. 2003). Long term survival of stably transduced epidermal cells in a graft can allow the secretion of exogenous gene products into the bloodstream (Cao et al., 2002, Pfützner et al., 2002, Rollman et al., 2003).

Several barriers presently exist that have impeded this technology from moving into the clinical arena. First is the ability to fabricate these "smart" grafts in a more efficient and robust manner, i.e. to develop a more highly proliferative and expanding cell population. Second is the ability to isolate a stem/progenitor cell, thus making gene therapy more practical by achieving high-level gene expression in a significant percentage of cells. Lastly, if stem cells are to play a role in clinical therapies the cells should not come into contact with foreign or undefined proteins (animal serum or feeder layer cells, or pituitary extract) in order to gain FDA acceptance.

The ability to isolate an epidermal stem cell for use in fabrication of autologous grafts would result in a more robust engineered construct capable of a higher level of gene expression in a significant percentage of cells, thus creating a more predictable graft success and functionality for long term use as a vehicle for gene delivery (Bianco and Robey, 2001, Ortiz-Urda et al., 2002, Chen M et al., 2002). The development of an ex vivo produced oral mucosa equivalent, using an oral keratinocyte progenitor/stem cell-enriched population, with long-term in vitro growth properties, that persist in vivo and forms a fully differentiated epidermis (Kolodka et al., 1998), would allow the generation of a more robust and functional EVPOME that has a higher proliferative capacity and longer life-span. To our knowledge, the identification, isolation and fabrication of human oral mucosal grafts with human oral keratinocyte stem cells has not occurred.

Substantial scientific and ethical challenges remain. In addition, much controversy remains over the sources of biological materials for stem cell research. Thus an unmet need remains for additional sources of stem cells that avoid or mitigate these and other issues.

SUMMARY OF INVENTION

To meet this unmet need, the present invention comprises compositions, methods, and systems for preparation of stem-cell enriched cell populations from sources of biological materials by sorting cell types according to size. Among other possible uses, such cells may be used in the fabrication of an ex vivo produced oral mucosa equivalent ("EVPOME") and as a target for insertion of genetic material for use in transmucosal gene therapy.

In accordance with some embodiments of the invention, oral keratinocytes were cultured in a chemically defined serum-free culture system, devoid of a xenogeneic feeder layer and bovine pituitary extract (as only one example, without limitation, Epilife medium with EDGS additives (Cascade Biologics, Portland Oreg., USA)). The cells were then sorted by relative cell size (for example, by diameter) into three groups, LG (large), MD (medium), and SM (small), by fluorescence-activated cell sorting ("FACS"), among other methods of sorting cells by relative size known to those of ordinary skill. Cells were characterized by immunolabeling, pre-FACS, for integrin $\beta 1$ and $\alpha 6$, and, post-FACS, for nuclear transcription markers, p63 and peroxisome proliferators-activated receptor-gamma ("PPAR$\gamma$"), as well as a cell cycle analysis. Primary non-cultured oral keratinocytes were used as a reference standard. Post-FACS, culture cells were assayed for their adhesion to type IV collagen, colony-forming efficiency, and long-term proliferative potential and their ability to regenerate an EVPOME, to assess whether they possess characteristics consistent with stem cells.

Our investigation and results showed that cells cultured in vitro were almost all $\beta 1$ integrin and p63 positive. SM cells demonstrated the highest colony-forming efficiency and long-term proliferative potential, as well as lowest PPAR$\gamma$ expression. In addition, the proportion of SM cells in G0/G1 decreased over days in culture concomitant with an increase in cell size. SM cells were the only group to successfully regenerate an EVPOME.

Thus, we have discovered that small-sized cultured oral mucosa keratinocytes possessed the phenotypic markers, characteristic cell cycle profile, and self-renewal potential that identify them as a progenitor/stem cell. In accordance with the invention, the use of a defined culture system and the physical isolation of a stem cell-enriched population allows incorporation of these cells into a tissue engineered EVPOME in a manner consistent with guidelines for fabrication of combinational cell devices. It also allows the use of such cells for any other use known to those of ordinary skill in the art.

Other aspects of the invention will be apparent to those skilled in the art after reviewing the drawings and the detailed description below.

BRIEF DESCRIPTION OF THE DRAWINGS

The present invention will now be described, by way of example, with reference to the accompanying drawings, in which.

DETAILED DESCRIPTION

Figure 1:
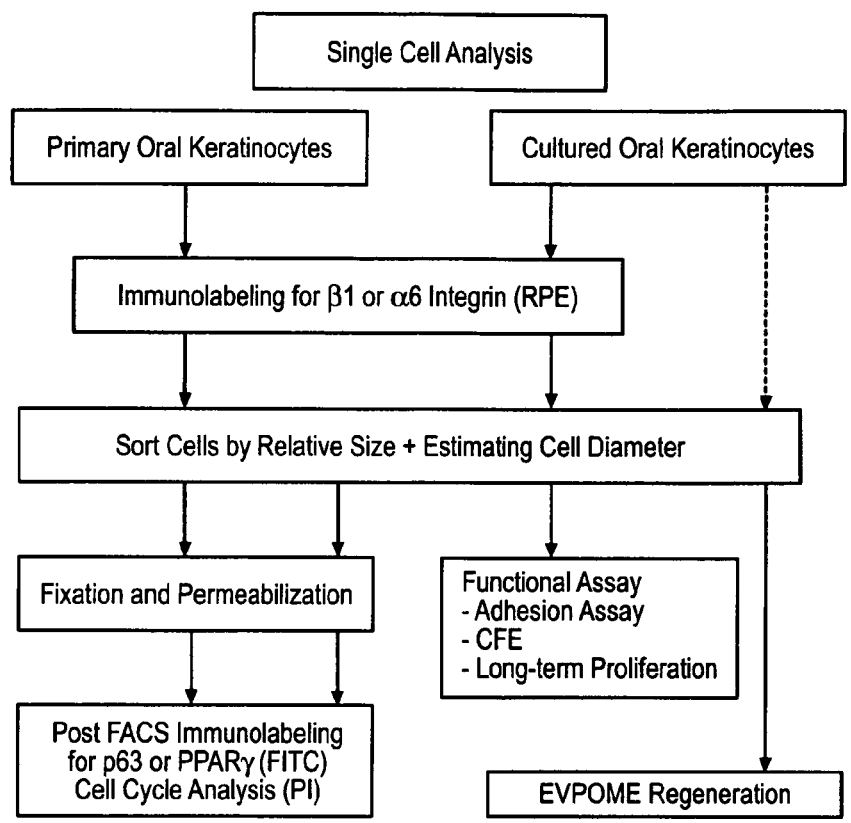
FIG. 1 is a flow diagram showing an overview of one embodiment of the invention, without limitation.

Referring generally to FIGS. 1-17 and without limiting the scope of the embodiments, the invention comprises compositions, methods and systems for preparation of stem-cell enriched cell populations from sources of biological materials in accordance with characteristics relating to cell size. In accordance with the invention, oral keratinocytes were cultured in a chemically defined serum-free culture system, devoid of a xenogeneic feeder layer and bovine pituitary extract. The cells are then sorted by relative cell size (diameter) into three groups; LG (large), MD (medium), SM (small) by fluorescence-activated cell sorting ("FACS") and other methods of cell sorting known to those of ordinary skill.

The cell source currently used most often to isolate primary uncultured human keratinocyte stem cells has been neonatal foreskin. (Li et al., 1998, 2004) However, neonatal foreskin cells are unavailable in an older population in need of reconstructive surgery or regenerative therapeutic medicine. In order to achieve the sufficient number of cells for use in graft fabrication, as well as for other uses, it is thus necessary to amplify the cells in vitro until appropriate numbers have been accumulated.

Epidermal stem cells have been identified using two basic strategies, first, through the use of cell surface molecular markers that allow FACS selection and, second, by functional analysis (Jones and Watt, 1993). The first and still most useful surface marker of human epidermal cells is β1-integrin, which are receptors bound to the extracellular matrices (Jones and Watt, 1993, van Rossum et al., 2002). Investigation by Li et al. (1998) demonstrated the identification and isolation of human stem cells based on the combination of other cell surface markers, $\alpha_6$ integrin and CD71. In addition, the differential adhesiveness on type IV collagen coated dishes has also been a means in which to enrich for epidermal stem cells (Tiberio et al., 2002). It has been shown, though, that once skin keratinocytes stem cells are place into culture, their characteristics are altered because they have been removed from the influence of the "in vivo niche" (Lavker and Sun, 2000).

An analysis of the growth potential of human skin keratinocytes by Barrandon and Green (1985, 1987) revealed three different types of cells based on the size of the clones they are capable of generating in a single plating. Holoclones, the smaller sized keratinocytes, smaller than 11 μm, had the greatest proliferative potential, and contained cells that almost all (95%) go on to form proliferative colonies on passaging. In addition, these cells were thought to express the nuclear transcription factor, p63, which is associated with cell proliferation (Pellegrini et al., 2001).

Another transcription factor, peroxisome proliferators-activated receptor γ ("PPARγ"), has been noted to increase as epithelial cells increased in their differentiation (Mao-Qiang et al., 2004; Westergaard et al., 2001). It was speculated that the holoclone-generating cells in vitro might be the stem cells in vivo. Others as well noted that the smaller sized skin cells, both in vivo and in vitro, had stem cell characteristics (Li et al., 2004, Youn et al., 2004) and that the size of cultured oral keratinocytes increased as their proliferative potential decreased, a sign of differentiation or senescence (Kang et al., 2000).

In accordance with the invention, we hypothesized that a culture of smaller-sized keratinocytes could contain the progenitor/stem cell subpopulation. Thus, we have developed and utilized phenotypic markers and functional assays to identify an oral mucosal progenitor/stem cell population consistent with these limitations. In doing so, we identified a small cell subpopulation that was highly clonogenic and had long-term proliferative potential, consistent with progenitor/stem cell features. In addition, we demonstrate that SM cells in later passage were only able to generate a highly-organized epithelial layer within EVPOME. In accordance with the invention, expanded cultures of an enriched population of oral mucosa progenitor/stem cells, under chemically defined conditions, may support greater advances in cell replacement therapy and other uses of stem cells known to those or ordinary skill in the art.

EXAMPLES

The following examples are provided without limiting the scope of the invention to only those discussed specifically herein.

Procurement of Human Oral Mucosa

Oral mucosa was obtained from oral and maxillofacial surgery patients undergoing tooth extraction, minor dentoalveolar surgery, or major maxillofacial surgery. The protocol for harvesting human oral mucosa tissue was approved by a university internal review board.

Antibodies for Staining

Mouse monoclonal antibodies used are listed in Table 1. For flow cytometry, the secondary antibodies used were FITC-conjugated goat anti-mouse $IgG_{2a}$, RPE-conjugated goat anti-mouse $IgG_1$ and $IgG_{2a}$ (Caltag Laboratories, Burlingame, Calif., USA). Isotype-matched normal mouse IgGs were used as negative controls (Santa Cruz Biotechnology, Santa Cruz, Calif., USA).

TABLE 1

| Target Antigen | Dilution Used | Clone | IgG | Source |
|---|---|---|---|---|
| Immunohistochemistry | | | | |
| β1 integrin | 1:100 | K20 | 2a | Santa Cruz Biotechnology (Santa Crutz, CA, USA) |
| p63 | 1:150 | 4A4 | 2a | Pharmingen (San Diego, CA, USA) |
| PPARγ | 1:100 | E8 | 1 | Santa Cruz Biotechnology |
| Flow cytometry | | | | |
| β1 integrin | 4 μg/10⁶ cells | K20 | 2a | Immunotech (Marseille, France) |
| +6 integrin | 2 μg/10⁶ cells | BQ16 | 1 | Santa Cruz Biotechnology |
| p63 | 0.5 μg/100 μL | 4A4 | 2a | Pharmingen |
| PPARγ (FITC) | 0.6 μg/100 μL | E8 | 1 | Santa Cruz Biotechnology |

Primary Keratinocytes

Oral mucosa tissue was treated overnight with 0.04% trypsin (Sigma, St. Louis, Mo., USA) at room temperature, and then transferred into an excess amount of 0.0125% trypsin inhibitor (DTI, Cascade Biologics, Portland Oreg., USA). The epithelial layer was scraped off from submucosal tissue with scalpel and dissociated. Single cell suspension was filtered through a 240 μm mesh (PGC Scientifics, Frederick, Md., USA), centrifuged at 1000 rpm for 5 minutes and resuspended in an appropriate solution depending on later experiment.

Immunohistochemistry

Unsorted oral mucosa keratinocytes (passage 2) were seeded onto AlloDerm®, and a day 11 EVPOME (D11E) was fabricated by our standard protocol (see U.S. patent application Ser. No. 10/281,940, filed Oct. 28, 2002, which is hereby incorporated by reference) with a chemically defined serum-free culture medium, Epilife® (Cascade Biologics) as described previously (Izumi et al. 2003). Native, non-cultured oral mucosa tissue and D11E were processed for routine histology. Immunostaining with β1 integrin, p63 and PPARγ was performed as described previously (Izumi et al., 2000), except for antigen unmasking procedure for β1 integrin. Sections were heated by microwave in a 1 mM EDTA (Sigma) solution, at pH 1.5-2.0, for 5 minutes×3 in a coplin jar (Shi et al., 1997).

Keratinocyte Culture and Preparation for Fluorescence-Activated Cell Sorting ("FACS")

Oral keratinocyte cultures were developed as previously reported (Izumi et al., 2000). Single cell suspension of primary keratinocytes was resuspended in Epilife® supplemented with 0.06 mM calcium, 25 μg/mL Gentamycin (Life Technologies, Gaithersburg, Md., USA) and 0.375 μg/mL Fungizone (Life Technologies), and then seeded into T-25 flasks at cell density of up to $5\times10^6$. Once cells reached 70-80% confluence, cells were detached in 0.025% Trypsin/EDTA (Cascade Biologics) for 15 minutes. After DTI was added, the cell suspension was transferred to a new flask at a density of a $1.5\text{-}2.5\times10^4$ cells/cm² for continued propagation. For FACS, oral keratinocytes from either primary tissue or serial cultures were resuspended in staining buffer (10⁶ cells/mL) (1% bovine serum albumin (BSA) (FisherBiotech, Fair Lawn, N.J., USA) and 0.1% $NaN_3$ in HPSS without phenol red, $Ca^{2+}$ and $Mg^{2+}$ (Cambrex Bio Science, Walkersville, Md., USA)).

Pre-FACS Immunolabeling for β1 and α6 Integrins

A summary flow chart of some embodiments of the invention, without limitation, is shown in FIG. 1. All procedures were not always performed with the same cell population because of the small tissue sample that was harvested from donors. In primary and some cultured oral keratinocytes, cells in staining buffer were incubated with anti-β1 or α6 integrin for 30 minutes on ice. After washing cells by staining buffer, they were resuspended in 100 μL staining buffer and incubated with 5 μL of RPE conjugated goat anti-mouse $IgG_{2a}$ or $IgG_1$ for 30 minutes. After washing thoroughly, propidium iodide (PI) (50 μg/mL, Sigma) was added for viability gating. Cells were kept in PBS on ice until FACS. RPE fluorescence was analyzed by FACA Vantage SE (Becton Dickinson Inc., San Jose, Calif., USA) during cell sorting.

Cell Sorting by FACS

Cells were sorted into three groups on the basis of "relative" forward scatter ("FSC") by using a FACA Vantage SE. From a scatter plot showing the FSC and side scatter (SSC), three gates were set to sort cells in equal proportion after eliminating cell debris and PI positive, non-viable cells (15-30%). Sorted cell groups are referred to as "LG (large)", "MD (medium)" and "SM (small)". Based on the isotype-matched IgG background control, percent total of β1 or α6 integrin (RPE) positive cells were determined. Mean FSC value of each sorted cell groups as well as three microbeads 15.41 μm, 21.14 μm, (Bangs Laboratories, Inc., Fishers, Ind., USA) 30.0

μm (Polysciences, Inc., Warrington, Pa., USA) for calibration was obtained every cell-sorting. A linear equation line ($R^2 > 0.99$) was made by plotting three FSCs and diameter of beads to estimate average cell diameter size in each group.

Post-FACS Immunolabeling for Nuclear Transcription Markers

Retrieved cells in which debris and PI positive cells were eliminated were fixed and permeabilized with 70% ice cold ethanol and kept at −4° C. for PPARγ immunolabeling and cell cycle analysis. Samples were rinsed with wash buffer (2% BSA and 0.1% $NaN_3$ in HPSS) and incubated with FITC conjugated anti-PPARγ for one hour on ice, followed by incubation with PI (10 μg/mL) and ribonuclease A (100 μg/mL, Sigma) for 30 minutes at 37° C. Trout Erythrocyte Nuclei (Biosure, Grass Valley, Calif., USA) was used for internal control. Some sample cells were fixed with 1% paraformaldehyde solution and kept at 4° C. for p63 staining. After washing with staining buffer, 10% normal mouse serum (Dako Corporation, Carpinteria, Calif., USA) was used to block nonspecific binding. Samples were incubated with anti-p63 for 40 minutes on ice, followed by incubation with 5 μL of FITC conjugated goat anti-mouse $IgG_{2a}$ for 40 minutes on ice. Samples were stored at 4° C. and analyzed within 4 hours by FACS. FACS was performed using an Epics Elite Flow cytometer (Coulter Cytometry, Hialeah, Fla.). Cell aggregates were eliminated from DNA analysis based on the ratio of integrated to peak fluorescence of PI. Data were collected on a logarithmic scale for FITC and on a linear scale for PI, and stored in Listmode. Based on the background control, percentages of PPARγ and p63 (FITC) positive cells were determined.

Stem Cell Functional Assays (I) Adhesion Assay $5 \times 10^3$ sorted, retrieved oral keratinocytes from each cell size group were plated onto 60 mm culture dish with 2 mm grids (Falcon, Franklin Lakes, N.J., USA) pre-coated with 100 μg/mL human type IV collagen (Sigma) for overnight at 4° C. They were allowed to attach for 20 minutes and non-adherent cells were removed. Attached cells were fixed 24 hours later with methanol, stained with 2% crystal violet (Baker Chemical, Phillipsberg N.J., USA), and counted under microscope. This assay was done in triplicate.

(II) Colony Forming Efficiency (CFE):

$5 \times 10^3$ sorted, retrieved cells were plated onto the well in 6-well plate (Coster, Corning, N.Y., USA) and cultured another 7 days. Culture medium was changed after 4 days. Cells were fixed and stained in the same way as the adhesion assay. Both colonies constituted of 16-49 cells and colonies with greater than 50 cells were counted separately. This assay was performed 6 times.

(III) Long-term In Vitro Proliferative Potential Assay $2.0 \times 10^4$ sorted, retrieved cells, from passage 4 to 6, were plated onto 60 mm culture dish with 2 mm grids, pre-coated with type IV collagen. They were allowed to attach for 20 minutes and non-adherent cells were removed. Adherent cells, referred to as passage one in this assay, were subcultured when the diameter of one of the consolidated colonies reached 10 mm. Harvested cells were seeded on to another culture vessel at the seeding density of $1.0 \times 10^4$ cells/$cm^2$. At 50-60% confluence, long-term culture was pursued until cell growth was exhausted. The assumptive total cell output, number of passages and duration of culture after plating were determined.

Fabrication of Ex Vivo Produced Oral Mucosa Equivalent (EVPOME)

Sorted, retrieved cells from passage 8 (highest generation prior to sorting), were used to assess their ability to generate an EVPOME per our standard protocol (Izumi et al, 2000).

Statistical Analysis

Data from assays was assessed using either repeated measures analysis of variance (ANOVA) adjusted with Tukey's adjustment or a regression analysis followed by a linear mixed model. Poisson regression analysis, in place of repeated measured ANOVA, was used for the data not showing normal distribution (Table 2).

Table 2. Statistical Measurement and Outcomes.

TABLE 2

Statistical measurement and outcomes.

| Subject for observation (Repeated Measures ANOVA) | Overall Outcome | Multiple comparison | | |
|---|---|---|---|---|
| | | LG vs MD | LG vs SM | MD vs SM |
| Proportion of p63 positive cells | NS | NS NS | NS | |
| Proportion of PPARγ positive cells | p < .0001 | p = .0009 | p < .0001 | p = .0027 |
| Adhesion assay | NS | NS | NS | NS |
| CFE (consisted of 16–49 cells) | p = .0001 | NS | p = .0001 | p = .0123 |
| CFE (consisted of more than 50) | p = .0049 | NS | p = .0038 | NS* |
| *Long-term in vitro proliferative potential assay | p = .0306 | NS | p < .0001 | p = .0020 |

| Subject for observation (Regression Analysis) | LG | Interaction MD | SM | Linear Mixed Model |
|---|---|---|---|---|
| Proportion of G0/G1 phase vs Age of patient | NS | NS* | NS | NS |
| Proportion of G0/G1 phase vs Days in Culture | p = .0148‡ | NS* | p = .0135 ¶ | p < .0001 |
| Proportion of G0/G1 phase vs Average Cell Diameter | p = .0023‡ | p = .0042‡ | p = .00165 □ | p = .0005 |

Figure 7A:
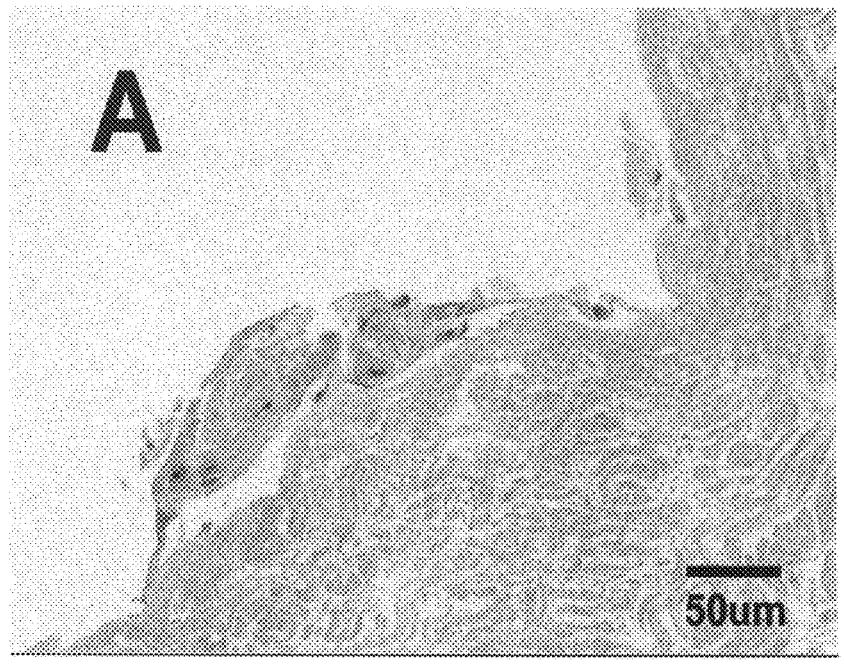
FIGS. 7A-C are photographs of an EVPOME fabricated by each size cell group sorted passage eight oral keratinocytes (HE staining)(A:LG cells, B:MD cells, C:SM cells)

*Poisson regression analysis.
NS not significant.
* close to significant
‡Slope is positive, □ Slope is negative as shown in FIG. 7A, B. NS; not significant
¶close to significant Results:

Demographics of studied samples were nine human males and eight human females (N=17). The ages of samples ranged from 11 years to 74 years, with a mean age±SD of 38.6±21.6 years. Of the seventeen samples, nine were analyzed at two different passages, for a total sample size of 26. Passages of each sample ranged from 1 to 8, with an average of 4.1±1.8. Days in culture ranged from 14 to 42 days with an average of 26.6±7.3 days. Procured were all from keratinized oral mucosa.

Non-cultured Primary Human Oral Mucosa Keratinocytes (I) β1 Integrin, p63 and PPARγ Expression in Native Oral Mucosa and EVPOME.

As summarized generally in FIG. 1, oral keratinocytes were harvested from discarded oral mucosa, cultured, and expanded in a chemically defined serum-free culture system, then sorted by relative cell size (diameter): Small (SM), Medium (MD), and Large (LG), with a FACScan flow cytometer (FACA Vantage SE, Becton Dickson, San Jose, Calif.) using size standard microbeads, 15.4, 21.1, (Bangs Laboratories, Inc., Fishers, Ind.) and 30.0 µm (Polysciences, Inc., Warrington, Pa.) in diameter. Cells were characterized pre- and post-FACS by immunolabeling for stem cell surface integrin marker, β 1 (beta 1) (clone K20, Santa Cruz Biotechnology, Santa Cruz, Calif.) and α 6 (alpha 6) (clone BQ16, Santa Cruz Biotechnology), and nuclear transcription markers, p63 (clone 4A4, Pharmingen, San Diego, Calif.) and PPARγ (gamma) (clone E8, Santa Cruz Biotechnology), and by performing a cell cycle analysis. Colony-forming efficiency and a long-term in vitro proliferation assay were also performed. Finally, each cell size group was assessed as to their potential to regenerate an EVPOME, which is the ultimate identifying test for a stem cell: "can it regenerate the tissue it originated from?"

Figures 2A, 2B:
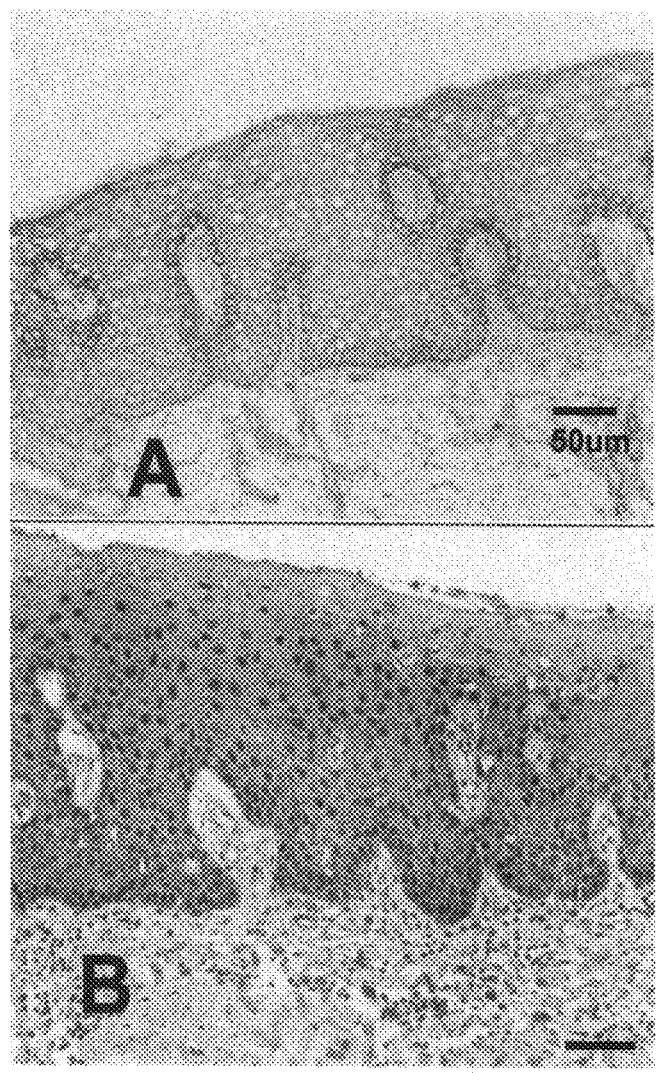
FIGS. 2A-F are photographs of immunohistochemical staining for β1 integrin, p63 and PPARγ in native, non-cultured oral mucosa (A: β1 integrin; B: p63; C: PPARγ; D: β1 integrin; E: p63; and F: PPARγ.
Figures 2C, 2D:
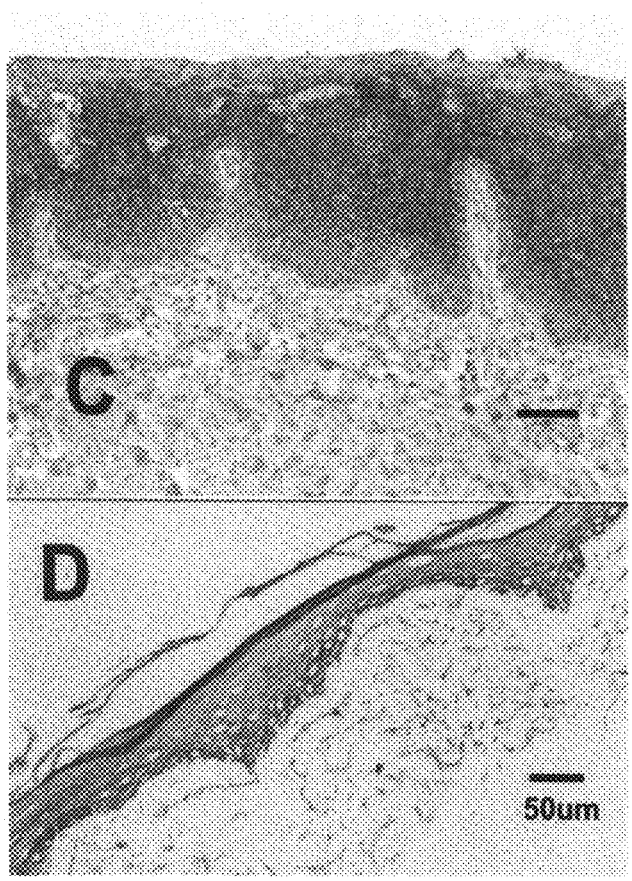
Figures 2E, 2F:
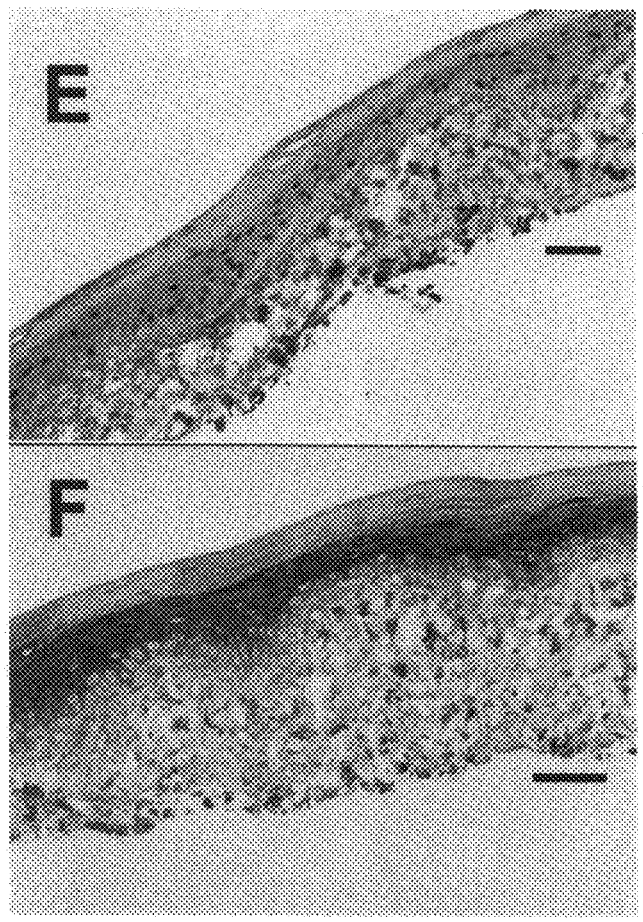

Through immunohistochemical staining, FIG. 2 shows the expression and location of β1 integrin, p63 and PPARγ in native, non-cultured oral mucosa (A: β1 integrin; B: p63; C: PPARγ; and our standard day 11 EVPOME (D: β1 integrin; E: p63; F: PPARγ). β1 integrin expression was confined to the basal layer of native oral mucosa (FIG. 2A) and was similar to distribution to that seen in human adult breast skin (data not shown). Staining was more intense in the basal cells and in some immediate basal cells at the top of the ridges, not the bottom of the ridges. p63 expression in nuclei was observed in the entire basal and suprabasal layers of native oral mucosa (FIG. 2B), implying that the suprabasal layer as well as basal layer in native oral mucosa may be hyperproliferative. PPARγ expression was seen in the suprabasal layers of native oral mucosa but was absent in the basal layer (FIG. 2C). This differential expression was more evident in the basal layer at the top of ridges. The PPARγ immunoreaction was mainly located in the cytoplasm with minimal nuclear staining. The EVPOME showed a similar pattern of expression of above markers as was seen in native oral mucosa (FIG. 2D-F). Thus, β 1 integrin was only expressed in the basal layer; p63 expression was throughout the basal and suprabasal layer; and PPARγ expression was seen only in the suprabasal layer and not in the basal layer, with a similar pattern seen in the tissue-engineered EVPOME.

(II) Single Cell Analysis in Non-cultured Oral Keratinocytes

The number of greater than $6 \times 10^7$ harvested allowed us to complete single cell analysis of primary, non-cultured oral keratinocytes. Sufficient primary oral keratinocytes were obtained from three native tissue samples. The average estimated cell diameter for LG, MD, SM cell groups was 33.77 µm, 20.25 µm, and 14.98 µm, respectively.

Figure 3:
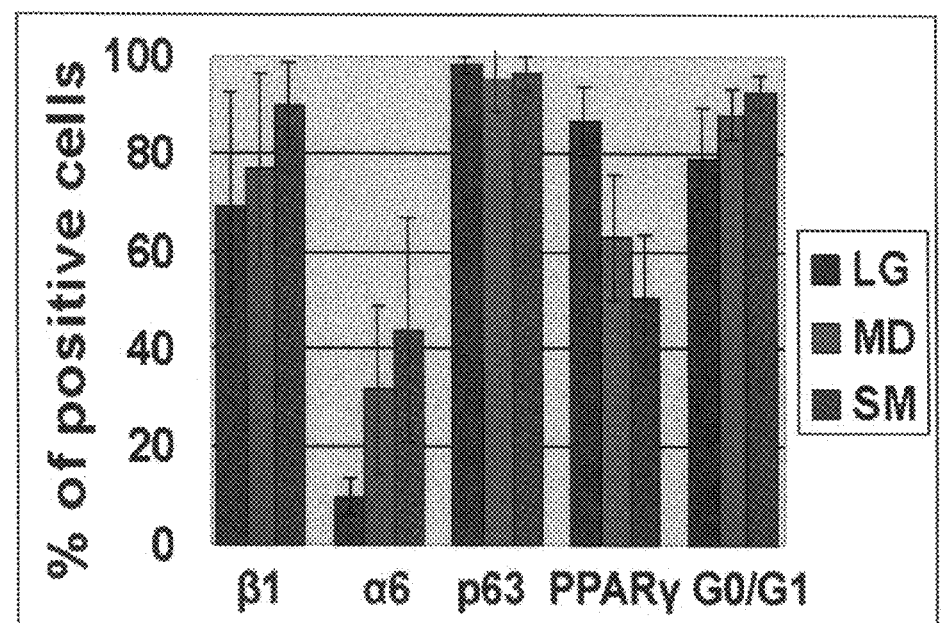
FIG. 3 is a chart of percentages of cells expressing β1 and α6 integrins, p63 and PPARγ in primary, non-cultured size sorted cells as well as that in G0/G1 phase in LG, MD, and SM cell groups.

FIG. 3 shows the percentage of cells expressing β1 and α6 integrins, p63 and PPARγ in primary, non-cultured size sorted cells, as well as that in G0/G1 phase in LG, MD, SM cell group. Data represents mean±standard deviation. All analyses were performed after eliminating debris and PI positive non-viable cells.

In primary cells, the small cell expressed integrin α6 and not PPARγ, consistent with a basal cell. The results for the medium cell were similar to the small cell and may represent a transit amplifying cell. All cell size groups were mostly integrin β 1 and p63 positive, consistent with a hyperproliferative mucosal gingival tissue. The small cell had a higher proportion in G0/G1 phase consistent with a slowly dividing "stem" cell. The percentage of viable single cells expressing β1 and α6 integrins decreased in order of cell size as 89.7% and 43.9% in SM cells, 76.6% and 31.6% in MD cells and 69.4% and 9.9% in LG cells, respectively. Fluorescent intensity did as well (data not shown). The majority of cells in each of the three size groups were p63 positive (FIG. 3). The LG cell group had a higher expression of PPARγ than either of the SM and MD cell groups. The majority of cells from all groups were in the G0/G1 (quiescent) phase of the cell cycle with the highest proportion present in SM cell group.

Figure 4A:
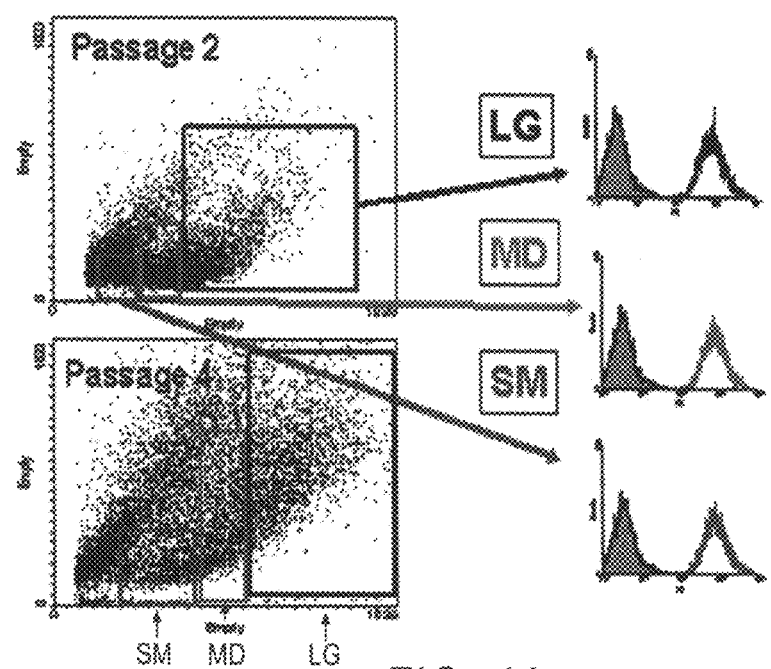
FIG. 4A is a representative scatter plot of cultured oral keratinocytes at passage 2 and 4.
Figure 4B:
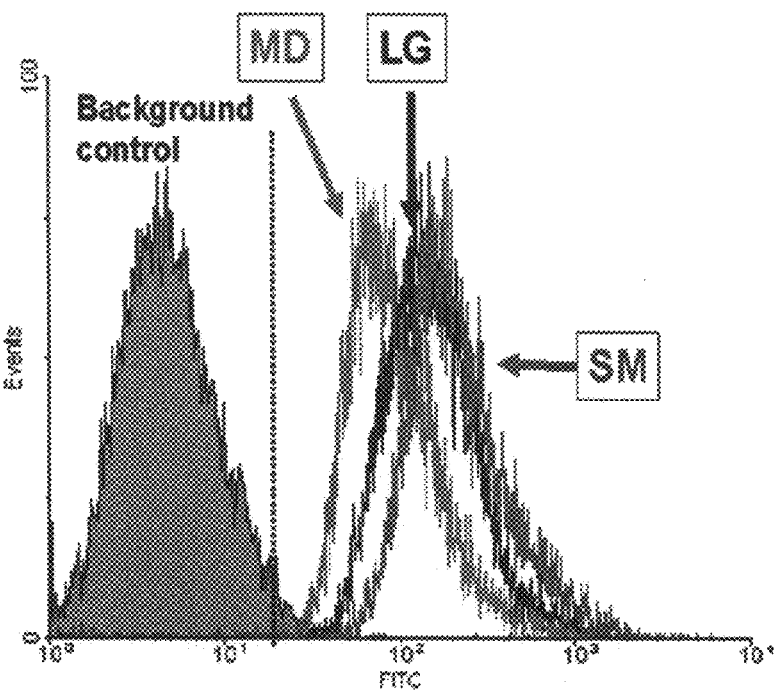
FIG. 4B is a plot of p63 expression at passage 3 in each size of sorted cells.

Cultured Primary Oral Mucosa Keratinocytes (I) Profiles of Unfixed, Cultured Oral Keratinocytes and Integrin Expression FIG. 4a is a representative scatter plot of cultured oral keratinocytes at passage 2 and 4 and three gates to sort cells by relative FSC (cell size in diameter) in an equal proportion. β1 integrin expression at passage 2 in each size sorted cells. The subpopulation (left of SM cells) in the plots was cell debris to be eliminated before sorting. FIG. 4b shows p63 expression at passage 3 in each size sorted cells. As shown in FIG. 4, cultured keratinocytes demonstrated an increase in cell size and granularity as the number of cell passage increased. The mean cell diameter of 18 sorted samples was 61.0±2.7 µm, 46.3±1.7 µm, and 33.9±0.9 µm for LG, MD and SM cell groups, respectively. More than 99% of cells in each size group were both β1 and α6 integrin positive (FIG. 4 and data not shown). In cultured cells, all size groups were β 1 integrin and p63 (+).

Figure 4C:
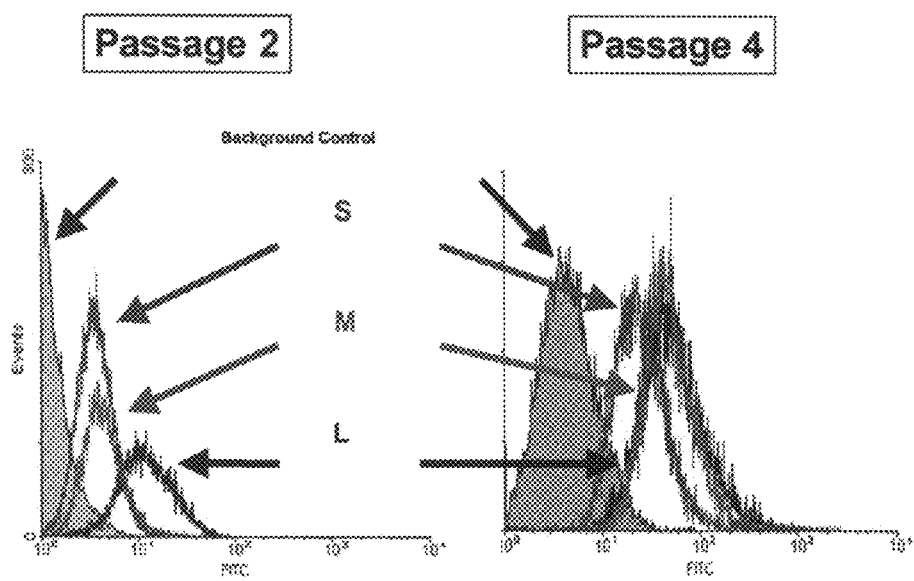
FIG. 4C shows PPARγ expression at passage 2 and 4 in each size of sorted cells.

(II) Profiles of Nuclear Transcription Markers p63 and PPARγ in Cultured Oral Keratinocytes The majority of keratinocytes in all cell size groups were p63 positive (FIG. 4B). p63 expression in SM cells had the highest fluorescent intensity (data not shown). All cell size groups showed an increase in percentage of PPARγ positive cells with increase in the number of passages (FIG. 4C, showing PPARγ expression at passage 2 and 4 in each size sorted cells). In cultured cells the LG cell had a higher expression of PPAR γ, consistent with a suprabasal, more differentiated, cell. As cells were subcultured, the higher number passages, 4, showed a higher expression of PPARγ consistence with cell senescence. Among the cell size groups, the proportion of PPARγ positive cells was highly statistically significant (Table 2). Based on cell cycle analysis of 17 samples, the mean proportion of cells in G0/G1 phase was 49.9±4.7%, 50.0±3.4%, 60.8±3.0%, for LG, MD and SM, respectively. Linear regression analyses between the proportions of cells in G0/G1 of each cell size did not correlate with "age of the patient", but correlated with "days in culture" and "cell diameter", and also showed a significant relationship between "days in culture" for LG and SM cells and for "cell diameter" in all three cell size groups (Table 2).

Figure 5A:
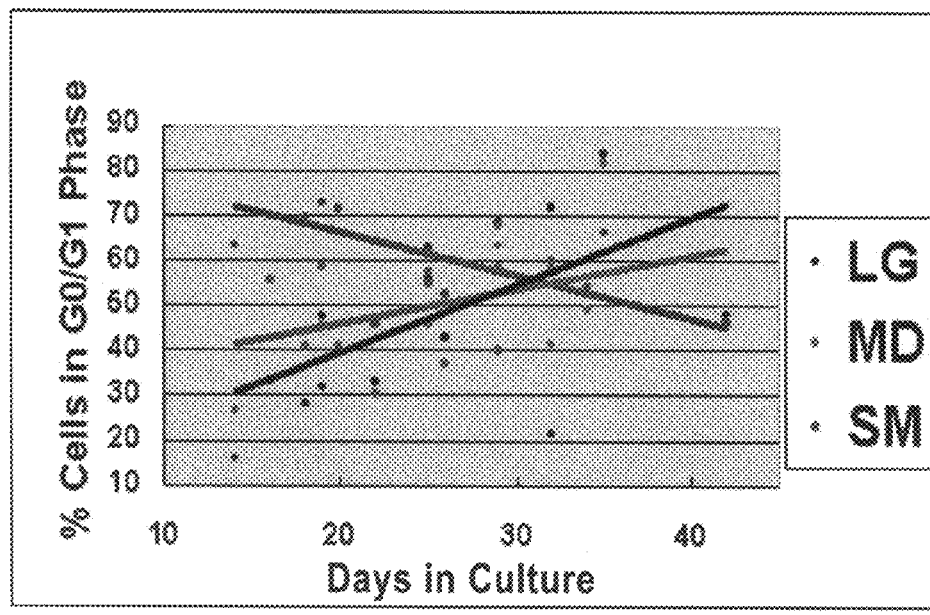
FIG. 5A is a linear equation showing the relationship between the proportion of cells in G0/G1 and days in culture in each size of sorted cells.
Figure 5B:
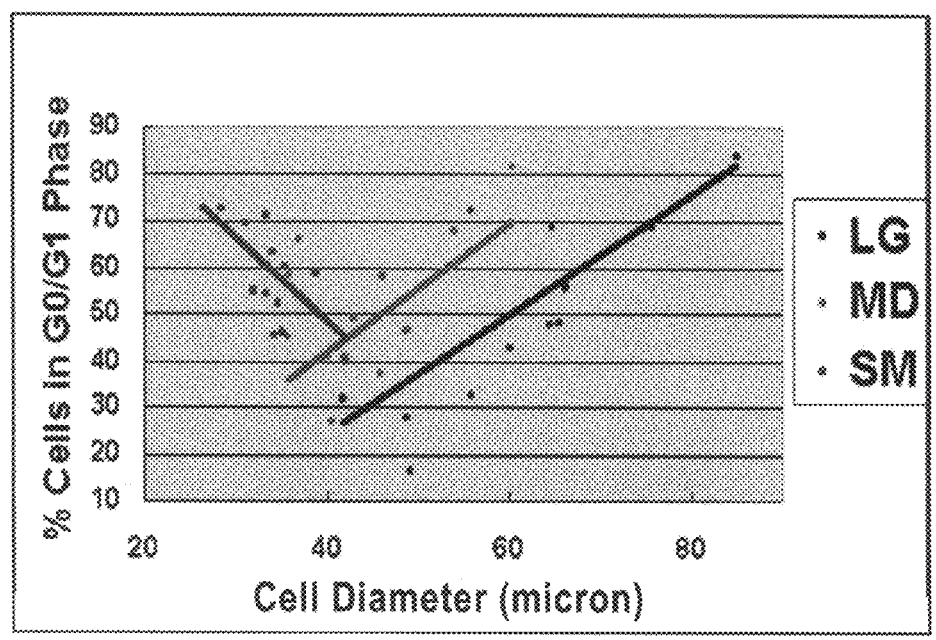
FIG. 5B is a linear equation analyzed by using a linear mixed model, showing the relationship between the proportion of cells in G0/G1 and cell diameter in each size of sorted cells

FIG. 5A shows a linear equation analyzed by using a linear mixed model, showing relationship between proportion cells in G0/G1 and days in culture in each size sorted cells. FIG. 5B shows a linear equation analyzed by using a linear mixed model, showing relationship between proportion cells in G0/G1 and cell diameter in each size sorted cells. FIG. 5 shows a linear regression analysis shows a positive slope for the large (LG) and medium (MD) cells consistent with a higher proportion in the quiescent G0/G1 phase correlating with an increase in cell size. In contrast, the small (SM) cell had a negative slope indicating a lower percentage of cells that were in the quiescent G0/G1 phase as these cells increased in size. (p=0.0005) Using a linear mixed model analysis there was a negative correlation of the percentage of cells in G0/G1 phase with an increase in cell size as well as a number of days in culture only in the SM cell group (FIGS. 5A, B) (Table 2). This would seem to indicate that the actively dividing transit amplifying cells emanate from the small "stem" cell.

(III) Stem Cell Functional Assays

Figure 6A:
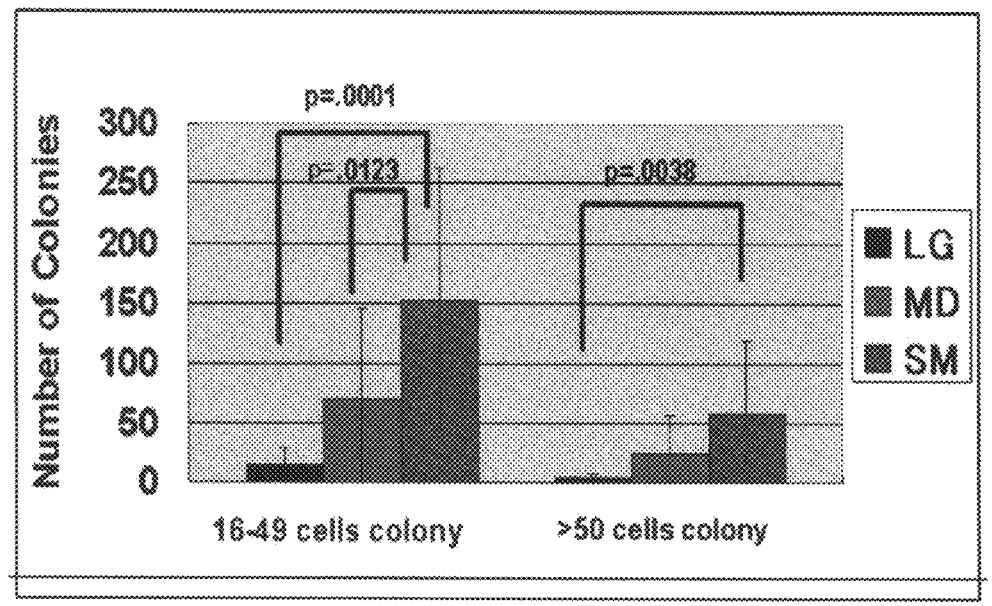
FIG. 6A shows colony-forming efficiency.
Figure 6B:
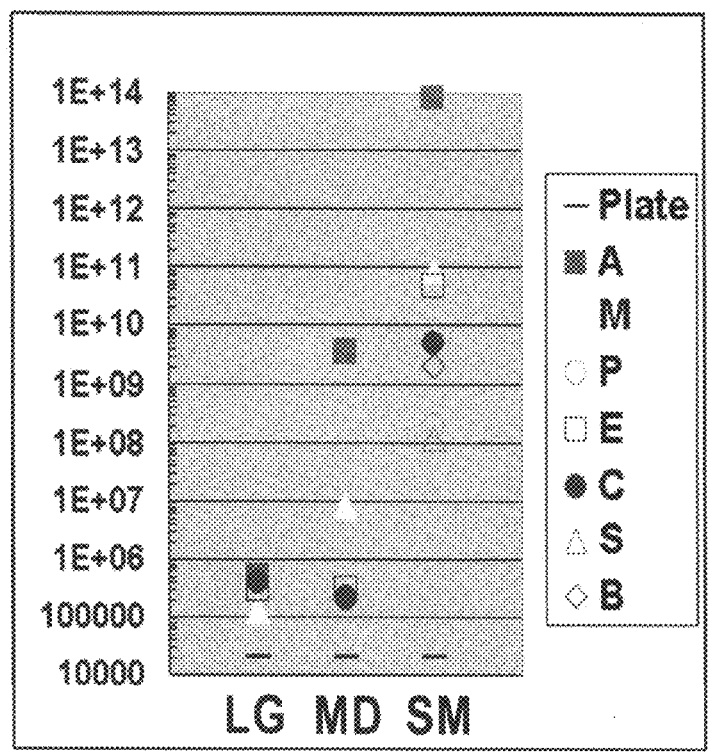
FIG. 6B shows results of a long-term in vitro proliferative potential assay in terms of total output of cells (y-axis).
Figure 6C:
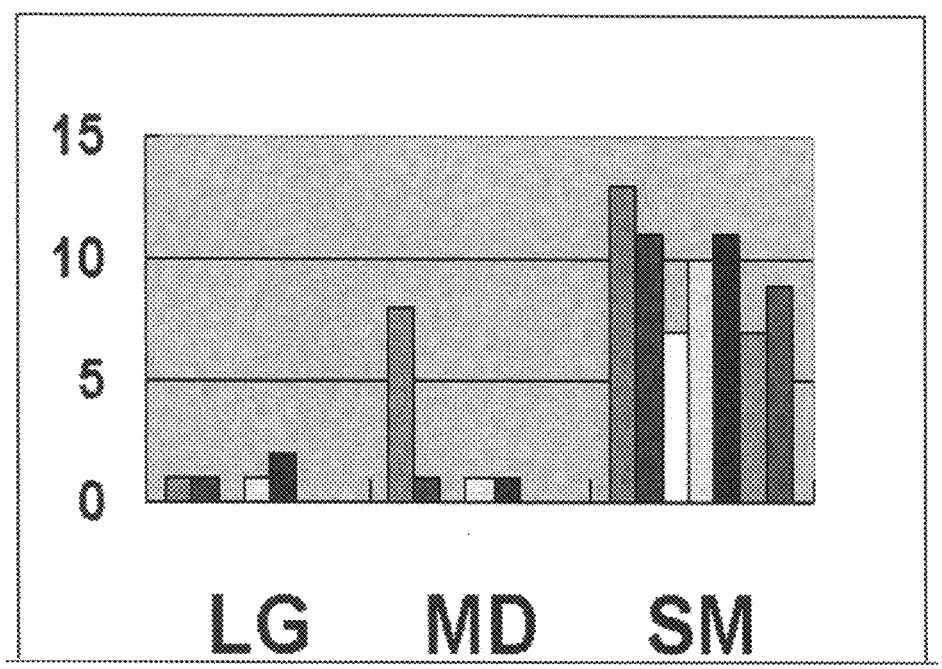
FIG. 6C also shows results of a long-term in vitro proliferative potential assay in terms of number of passages (x-axis).
Figure 6D:
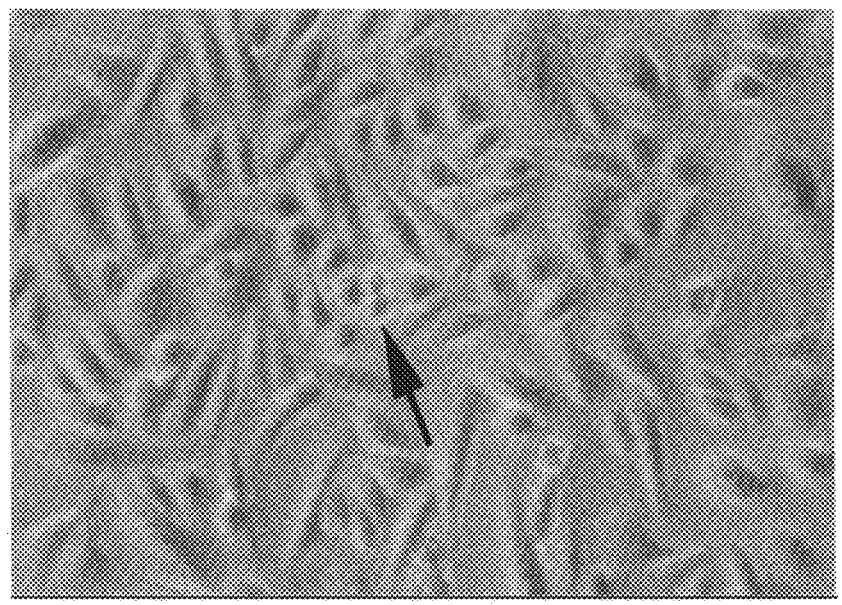
FIG. 6D is a phase contrast image of SM cells prior to passage five during the assay (200× mag.).
Figure 6E:
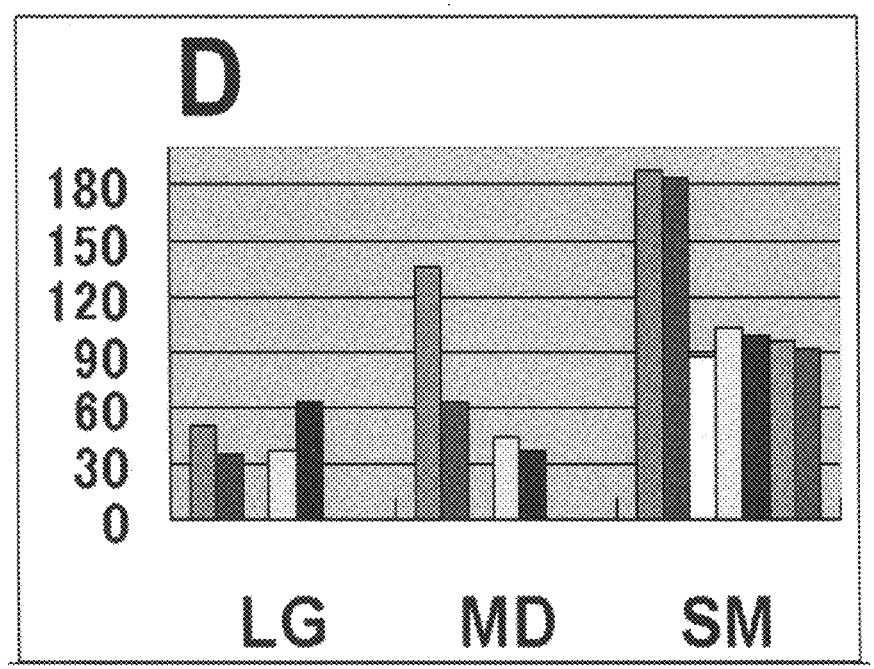
FIG. 6E shows a long-term in vitro proliferative potential assay in terms of duration of culture (y-axis=days in culture).

Type IV collagen adherence within 20 minutes was not significant between the three different cell size populations (data not shown). In contrast, the CFE and long-term in vitro proliferative potential assay showed a statistically significant capability of the SM cells to give rise to larger colonies (FIG. 6A), and have a greater proliferative potential (maintain their population doubling and enhance longevity) than either the MD or LG groups (FIGS. 6B, C, D) (Table 2). FIG. 6A shows colony forming efficiency. Left bars showed colonies consisted of 16-49 cells. Right bars showed colonies consisted of greater than 50 cells. FIGS. 6B, C, E shows long-term in vitro proliferative potential assay (1) Total output of cells. FIG. 6C shows long-term in vitro proliferative potential assay (2) Number of passages. The insert to FIG. 6D is a phase contrast image of SM cells prior to passage five during this assay. Smaller cells (arrow) emerged among cells that were initially plated and had increased in size. FIG. 6E shows long-term in vitro proliferative potential assay (3) Duration of culture. FIGS. 6A, B showed the SM cell group had the greatest potential to form colonies and had the ability to be subcultured through more generations than either the MD or LG cell groups (p=0.0306); this is consistent with the SM cell being a progenitor/stem cell.

(IV) Fabrication of Ex Vivo Produced Oral Mucosa Equivalent

Figure 7B:
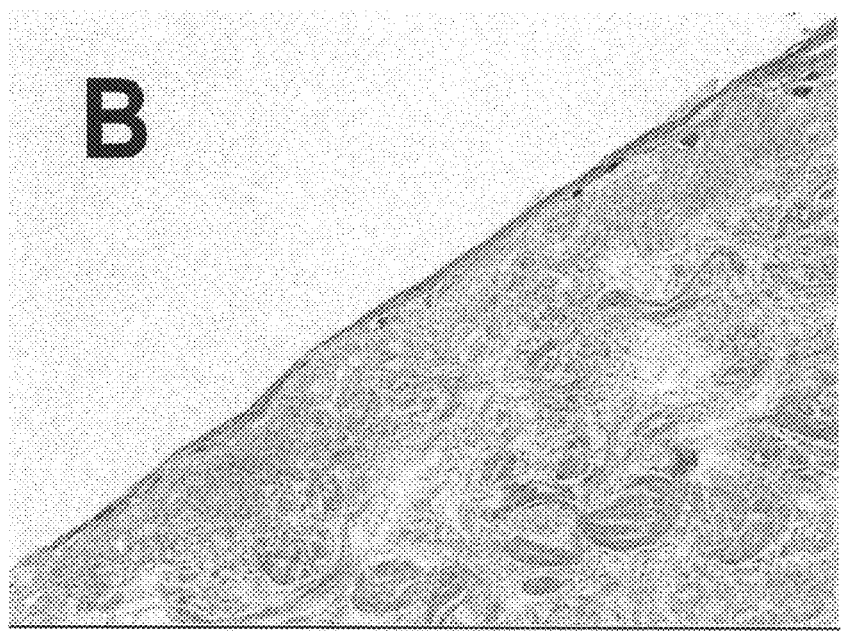
Figure 7C:
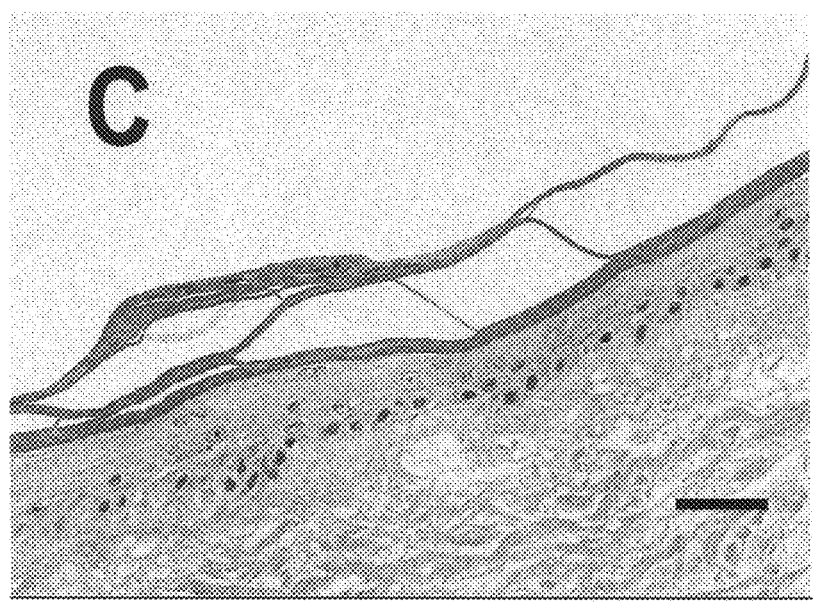

FIG. 7 shows an EVPOME fabricated by each size cell group sorted passage eight oral keratinocytes (HE staining) (A:LG cells, B:MD cells, C:SM cells) The LG cell group was not able to form a continuous layer while the MD cell group was capable of forming a poorly organized epithelial monolayer on the AlloDerm®. The SM cell group was the only group capable of regenerating a highly stratified and well-organized epithelial layer on the AlloDerm® (FIGS. 7 A, B, C).

As indicated herein, in accordance with the invention, we have isolated progenitor/stem cells to develop a transduced oral mucosa graft to reconstruct major oral defects secondary to oncologic resection, traumatic events or developmental disturbances, as well as for other uses known to those of ordinary skill in the art. The graft may act both as a tissue used for reconstruction and as a repository for in situ transmucosal delivery of recombinant growth factors, cytokines, or other substances. This route of administration is potentially more convenient and would have a more favorable pharmacokinetic and pharmacodynamic profile for many proteins (Hengge et al., 1998, Smart, 2004). It would also allow for the development of an easily regulated gene expression system (Pfützner et al., 1999, Pfützner et al., 2002, Cao et al., 2002, Rollman et al., 2003).

The epithelium or keratinocyte has been considered an attractive target tissue for gene therapy. First, it is easily obtainable and readily expanded from small tissue biopsies using defined culture system. Secondly, grafts of epidermis/mucosa can be transplanted with ease back to the host. Third, accessibility of the graft location allows the ability to monitor the graft. Fourth, epithelium is a constantly renewable tissue via its stem cell population. This gives the potential of ease of transfection/transduction and a guarantee of a sustained cell population. Fifth, the biology of the epithelium is relatively well defined at both the cellular and molecular levels. Sixth, the keratinocyte has been shown to be capable of synthesizing and delivering to the extracellular space a wide variety of gene products. Gene products of keratinocytes that have been shown capable of being delivered to the extracellular space include cytokines, enzymes, and adhesion molecules, which together constitute the majority of the regulatory environment of the epithelium (Vogel, 1993, Greenhalgh et al., 1994). The oral mucosa route has a distinct advantage over skin, its high degree of inherent vascularity (Greenhalgh et al., 1994).

A key to successful gene therapy using epidermal cells is the isolation of the putative stem cell in accordance with the invention that will confer sustained expression of the transduced gene. Most stem cell biologists refer to the bulge of the hair follicles containing biopotent follicular stem cells as they give rise to both keratinocytes of the hair follicle and the interfollicular epidermis (Potten and Booth, 2002, Niemann and Watt, 2002, Janes et al., 2002, Fuchs and Raghavan, 2002, Alonso and Fuchs, 2003). The oral epithelium, in comparison to skin, is quite unique in that it has a higher cell production rate with reduced turnover time in both keratinized and non-keratinized epithelium (buccal mucosa: 1-3 weeks) compared with the skin (range of 4-10 weeks depending on site) (Hengge et al., 1998, Winning and Townsend, 2000, Hata et al., 1995, Cutright and Bauer, 1967, Thompson et al. 2001, Weinstein et al., 1984). In addition, others have noticed that epithelial cells isolated from the oral mucosa are at a lower stage of differentiation than skin keratinocytes resulting in a higher rate of proliferation in vitro in the oral epithelia than in the epidermis (Hata et al., 1995, Gibbs and Ponec, 2000). We have also noticed that our EVPOMEs showed a keratinocyte population that was highly proliferative, more so than native keratinized mucosa (Izumi et. al., 2000). What makes these observations even more interesting is the fact that oral mucosa is devoid of adnexal structures thought to be the repositories of stem cells for the epidermis, thus making it a "large interfollicular area". This would seem to indicate that the stem cell population of oral keratinocytes lies within the basal layers of the mucosa, making them readily accessible for isolation (Lavker and Sun, 2000).

In our work, the characteristics of our non-cultured oral mucosa keratinocytes showed that the basal layer expression pattern of $\beta1$ integrin, as well as the lower level of suprabasal cells in native, non-cultured oral mucosa, was consistent with the previous reports seen in interfollicular epidermis and esophageal epithelium (Jones et al., 1993, Seery and Watt, 2000), suggesting to us that $\beta1$ integrin functions as an oral mucosa stem cell marker in vivo. In addition, the pattern of $\beta1$ integrin expression was similar to that seen in esophageal epithelium, with higher intensity at the top of the ridges (closest to the epithelial surface) in association with frequent Ki-67 positive cells and lower expression at the base of ridges (deepest from the surface) with less Ki-67 positive cells being present (Seery and Watt, 2000). The association of Ki-67 and $\beta1$ integrin expression pattern in oral mucosa was consistent with that seen in our previous study (Izumi et al., 2000).

The results with the single cell analysis further highlight β1 and α6 integrins functioned as stem cell markers in vivo in oral mucosa. The greater percentage of β1 integrin expression, even in the lowest in LG cells, is consistent with the study reporting extensive β1 integrin staining above the basal layer in normal oral mucosa (Jones et al. 1993) and the report concluded early terminal differentiated cells in the lower suprabasal layer cells also expressed β1 integrin (Kaur and Li, 2000). Although we did not investigate which layer of cells were eliminated by PI and subjected to FACS analysis, it is highly likely that basal layer zone derived keratinocytes were analyzed in this study. It was conceivable that the percentage of α6 integrin expressed cells was not as high as that of β1 expressed cells because basal layer keratinocytes in which stem and transit amplifying cells reside express β1 integrin on entire surface different from α6 integrin expression pattern of only basement membrane surface (Kaur and Li, 2000). Based on the percentage of cells expressed these integrins, basal keratinocytes predisposed to fall into SM and MD cells, in contrast, LG cells seemed to be from suprabasal cells.

The non-cultured SM and MD cells also showed a lower percentage of PPARγ expression when compared with LG cells which were PPARγ positive. This indicates that the majority of basal layer cells in which stem and transit amplifying cells should be located were sorted into SM and MD cell groups, while the suprabasal layer cells, which were PPARγ positive, were sorted into the LG cell group. The fact that PPARγ expression, which has been directly correlated with cell differentiation, was absent in the cells of the basal layer at the top and base of the ridges, is consistent with the presence of a stem cell population being present in native oral mucosa as well as the EVPOME.

p63 expression was seen in both the basal and most suprabasal layers of native mucosa tissue, which is known to have a highly proliferative epithelium (Koster and Roop, 2004). Single cell analysis of non-cultured cells is consistent with this finding, as was seen in native tissue. In addition, the highest fluorescent intensity in SM cells showed their highly proliferative potential (Parsa et al. 1999).

It has been previously reported that the majority of keratinocyte stem cells from primary tissue, both in human and mouse, are in a slow-cycling state because of the environmental cues originating from the in vivo stem cell "niche" (Nguyen et al., 2000), which maintains stem cells in a quiescent G0/G1 phase (Li et al., 1998, Kaur and Li, 2000, Dunnwald et al., 2001). Our data is consistent with this as we found that the SM cells were characterized by having the highest percentage of cells in G0/G1 phase.

According to our data, once primary oral keratinocytes are placed in culture, they appear to undergo a "homogeneous, phenotypic change" as they are released from the constraints placed on them by the niche that they live in in vivo (Lavker and Sun, 2000). The reduction of stem cell potential within stem cell lineage in vivo because of early occurrence of a critical cut off point would trigger this phenotypic modulation (Potten and Booth, 2002), resulting in a behavioral change to transient-amplifying cells with retaining "stemness", as noted by an increase in stem cell markers, β1 and α6 integrins as well as p63, and functional assays. This change is also correlated with an increase in cell size in comparison to their non-cultured in vivo counterparts (Lavker and Sun, 2000, Youn et al. 2004). This might be also a consequence of auto-selection of the oral keratinocytes being cultured in an environment devoid of serum and non-essential fatty acids which have been documented to enhance cell proliferation in an attachment-dependent cell culture system (Izumi et. al., 2000) making the markers used to identify stem cells in vivo not practical in vitro.

Through our invention, we have shown PPARγ expression and anatomical distribution in native and cultured oral keratinocytes for the first time. PPARγ expression cannot be used as a stem cell marker because it is an intracytoplasmic protein, however, the number of cells expressing PPARγ increased as keratinocytes increased in size and become more differentiated or senescent. Because of its correlation with cell differentiation, the ability to modify PPARγ expression through pharmacological or genetic manipulation might be a way in which to alter the differentiation pattern of oral keratinocytes in vitro. Although most studies demonstrated that the expression of PPARγ was localized in the nuclei (Westergaard et al., 2001; Kawakami et al., 2002), it was unexpected that it was localized in the cytoplasm in oral keratinocytes. There were reports on cytoplasmic expression of PPARγ in the inner root sheath of hair follicle and cancer cells (Jiang et al., 2000; Mössner et al., 2002). Nikitakis et al. (2002) showed the NSAID, sulindac, had an effect on oral squamous cancer cell growth inhibition with increasing PPARγ expression within the cytoplasm. Jiang et al. (2000) reported gamma linolenic acid induced translocation of PPARγ from the cytoplasm to the nucleus, suggesting some ligands incorporated via pinocytosis may act on the intracellular peroxisomes and move it to the nucleus. Our data showed that oral keratinocytes cultured in linoleic acid and arachidonic acid supplemented medium expressed PPARγ in both the cytoplasm and nucleus. Essential fatty acid (PPARγ ligands) deficiency in our culture system may therefore play a role in the localization of PPARγ expression.

Our in vitro keratinocyte features indicated that the characteristics of SM cells were consistent with those of an in vivo quiescent stem cell and significantly different from the NM and LG cell subpopulations. This was substantiated by the increase of cell proportion in G0/G1 phase, the highest CFE and the long-term in vitro proliferative potential as well as the lower PPARγ expression. During earlier days in culture, the proportion of cells in G0/G1 remained larger only in SM cells while the proportion cells in G0/G1 in MD and LG cells was relatively low. The negative slope of SM cells shown in FIG. 5A indicated that the proportion of cells in G0/G1 was on the decrease over days in culture. This is consistent with the hypothesis of stem cell lineage in which stem cells' division is considered to be asymmetric (Potten and Booth, 2002). A stem cell gives rise to a stem cell and a transit amplifying cell as a daughter cell, which would make the proportion of cells in G0/G1 decrease as an entire cell population over time relative proportion of proliferating cells increases. In contrast, a positive slope of both MD and LG cells indicated an increase of the proportion of cells in G0/G1 phase, which implied MD and LG cells were undergoing committed terminal differentiation over days in culture. As keratinocytes increased in size within each cell size group, the correlation between the proportion of quiescent cells and cell diameter was quite unique, negative as well, in SM cells (FIG. 5B). Thus, SM cells comprise a stem cell enriched subpopulation. In addition, this indicates that approximately 40 μm in diameter would be the critical size at which the cultured oral keratinocyte lose proliferative potential and enter into irreversible terminal differentiation.

Another property to substantiate SM cells as a stem cell enriched subpopulation was the in vitro functional assays; CFE and long-term in vitro proliferative potential, although no significant difference among cell sizes was noted in the adhesion assay. This discrepancy could be related to the high expression level of β1 and α6 integrins in all three cell size groups. SM cells were able to develop significantly larger, exuberant colonies than MD and LG cells, suggesting a growth potential arising from stem cells. It has been postulated that the fact that cells are able to generate large colonies does not necessarily correlate with their long term proliferative potential (Janes et al., 2002), but in our study this was not an issue since the SM cells also possessed a long term proliferative potential. (E.g., FIGS. 6C and 6E).

Significantly, our work showed that SM cells contained a progenitor/stem cell subpopulation was their ability to regenerate a fully-stratified and well-organized EVPOME whereas MD cells and LG cells were not able to do so. The regenerative capability as well as the long-term growth potential in SM cells is consistent with the recent study in which Kaur et al. (2004) proposed that the assessment of stem cell activity requires the development of long term assays that measure sustained epithelia tissue regeneration. The result in our work was distinct among cell groups. The discrepancy might be due to the technique used for fractioning cell population (cell size vs. marker expression) or the culture system used or the intrinsic characteristics of keratinocytes (tissue source, age) used.

The difference of the dot plots between the cultured palm keratinocytes as seen in Wan et al's study (Wan et al., 2003) and the cultured oral keratinocytes seen in our study, is that the larger size cell population showing a larger forward scatter (FSC) and side scatter (SSC) in their study lacked (FIG. 3A in Wan et al., 2003) when compared with our data (FIG. 4A). This difference may be attributed to culture conditions used a feeder layer and serum while our cells were never exposed to either of these materials. Moreover, according to Barrandon and Green (1985), cultured keratinocytes less than 20 μm in size from neonatal foreskin showed the clone-forming ability, whereas, in our study, cultured oral keratinocytes showing the clone-forming ability were twice as large on the average, <40 μm. This dichotomy in size may be also due to the presence of a feeder layer and serum in their culture environment. Based on both studies, keratinocytes taken directly from neonatal skin or oral mucosa were smaller in size than cultured keratinocytes.

In previous studies exploring stem cell biology of human keratinocytes, hematopoietic and embryonic stem cells (Amit et al., 2004), cells were grown in a system that allows the cells to come into contact with foreign materials which would negate their ability to be used in humans for tissue engineering or for gene therapy. Any cells that comes into contacted with foreign or undefined proteins (animal serum, feeder layer, or pituitary extract) prior to grafting to humans is not acceptable according to the guideline of Food and Drug Administration (FDA) or European Agency for the Evaluation of Medicinal Products (EMEA) although there have been no reports on adverse events caused by foreign materials (Louet, 2004). In our work, we have successfully isolated a progenitor/stem cell enriched population from cultured primary oral mucosa keratinocytes by sorting cells by physical means, as one example only, by cell diameter, using a FACS in a serum- and feeder layer-free system without the use of pituitary extract using a protocol that is within the guidelines established by the United States Food and Drug Administration (FDA) for use in humans (Izumi et al., 2004). Adhering to these guidelines, this technique should allow participation in clinical trials under good manufacturing practice standards.

In summary, in accordance with some embodiments of the invention, without limitation, the progenitor/stem cell enriched population isolated was at largest 40 microns in diameter, expressed β1 and α6 integrins and p63 nuclear transcription factor, both hallmarks of epithelial stem cells. In addition, they had a high colony forming efficiency, a long-term proliferative potential, and cell cycle analysis that showed them to be in a relative quiescent state of division. The progenitor/stem cell enriched population had a low level of expression of nuclear transcription factor, PPARγ, which would indicate that the cells are in an undifferentiated state. Compelling evidence for the SM cells to be progenitor/stem cells was their ability to regenerate an EVPOME that was identical to that accomplished with unsorted earlier passaged, cultured cells.

In accordance with some embodiments, without limitations, the invention comprises the development of oral mucosa substitutes to address the deficiency of oral mucosa available for intraoral reconstruction. Thus, in some embodiments, the invention comprises methods to isolate and characterize oral mucosal stem cells that could be used for more efficient fabrication of an EVPOME and as a target for insertion of genetic material for use in transmucosal gene therapy with the EVPOME.

The SM cell population possesses the phenotypic markers, cell cycle characterization, functional assays and ability to regenerate an EVPOME that would characterize them as oral mucosal stem cells. In addition, our studies are done in an environment that is consistent with FDA regulatory guidelines for combinational cell-based products of which tissue engineered oral mucosa falls under. Adhering to these guidelines at the beginning of the development of a "smart" EVPOME will allow us to move into the clinical arena in a more timely and efficient manner.

In some embodiments, without limitation, the invention comprises compositions, methods and systems to prepare and grow putative stem cells from adult human epidermal tissue with separation by methods in addition to FACS. As one example only, without limiting the scope of the invention, routine and standard culture of primary keratinocytes from skin involves the separation of epidermis from dermis using a pancreatic enzyme called trypsin, which is a neutral protease. Trypsinization splits the skin at the dermal/epidermal junction, releasing the basal cells of the epidermis. These are freed from the epidermis and dermis by gently scraping with a sterile forceps. The cell suspension is collected, put through a large mesh filter, centrifuged, re-suspended in growth medium plus 2% serum (for primary attachment only), and placed into plastic growth vessels with a specially treated plastic bottom. The cells attach to the plastic and form a monolayer. The cells are fed serum-free medium. The cells grow to cover the bottom, usually to 70% of the surface area (called 70% confluence). The cells are fed every second day with standard amount of medium. A T-flask with a 25 cm sq growth surface, called a T-25 flask, holds 5 ml of medium; a T-75 flask holds 15 ml of medium, etc. The medium is Epilife medium, plus EDGS additives, which replace bovine pituitary extract with transferrin and bovine serum albumin.

When the monolayers reach about 70% confluence, they are passaged or split, using trypsin. The split is usually about 1 to 2. When treated with care, a primary culture can be passaged 6-10-times, at maximum, although the practical number is about 5 passages. The cells can be cryopreserved as well.

The epidermis is a family of cells. The literature describes more subdivisions of the three general types: stem cells, which are thought to be found more frequently in the deeper elements of the dermal/epidermal junction; progenitor or transitional cells, which are committed to differentiation but can undergo a number of divisions; and differentiated cells, which are in the business of forming the stratum corneum of the skin.

Using our procedure for culturing, it is thought that some stem cells are in the initial culture but are lost during culture growth and plating. The transitional cells form the bulk of these cultures, and they differentiate and eventually die. Confluence normally induces differentiation and cell death if the cells are not passaged.

In some embodiments of the invention, without limitation, the dermal component is initially processed according to methods known to those of ordinary skill in the art (for example, see Park, Kang, Kim et al, 2004). However, unlike other methods, in accordance with the invention, epidermal cells are removed from the dermal junction component by a second trypsinization step. In accordance with the invention, after completion of the initial processing, the dermal component, by way of one example only, from a 6 by 12 cm strip of skin, is further trypsinized with 100 ml of enzyme solution, at 37 deg C. with stirring for 45 min. The cell suspension is centrifuged without filtering and re-suspended in a flask to about 20 million cells in 15 ml of medium (plus about 2% serum). The flask has a coating, such as CellBind (Corning, Inc.), collagen of various types, fibronectin, or any specially treated tissue culture flask surface treatment, such as collagen "wash", a synthetic surface layer, or mechanical alteration such as rippling the surface to increase the growth surface.

Figure 8:
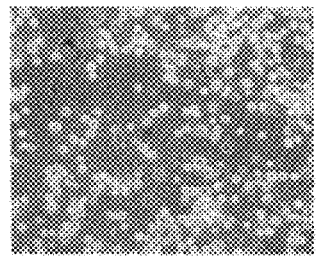
FIG. 8 is a photograph showing a primary culture suspension with normal plating density.

FIG. 8 shows an initial plating cell suspension of a primary culture suspension with normal plating density. The cell suspension is incubated for 15 minutes, during which time the cells attach and grow. Other attachment times, from 1 minute to 60 minute intervals or hours, can be used.

Figure 9:
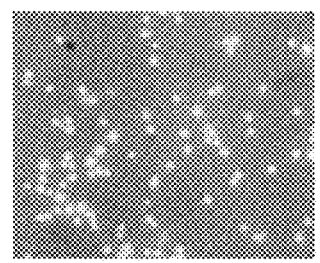
FIG. 9 is a photograph showing a primary cell culture after a 15 minute attachment period.

The flasks are then tilted, and the cell suspension is removed according to methods known to those of ordinary skill (for example, see Kim, Cho and Choi, et al, 2004). Serum-free medium is then added to the flasks with the adhering cells, and the attached cells are grown in the media. Any serum free, low calcium and fatty acid free medium can be used. (FIG. 9 shows a primary culture after a 15 minute attachment period on a CellBind (Corning, Inc., NY) plate).

The medium volume is about 3× normal, and the cells are fed every other day with 3× the normal amount of a serum-free, low calcium, fatty acid free medium, a volume that is a close fit for the flasks.

Figure 10:
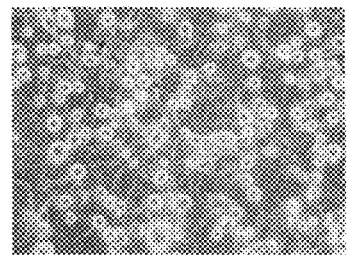
FIG. 10 is a photograph showing dermally derived keratinocytes initially attached as a primary culture for 1 hour, after 17 days of growth as a monolayer.

The few attached cells form colonies which quickly grow to form monolayers, that is, approximately 200,000 cells will fill a T-75 flask in about 5 days (1.5 to 2 million cells) (See FIG. 10, which is a photograph showing dermally derived keratinocytes, initially attached for 1 hour, after 17 days of growth as a monolayer. Rounded cells are lifting off the monolayer into the culture medium.) As shown in FIG. 10, a cell culture after 2 weeks of growth, numerous cells are floating in the medium. These cells can be transferred in spent or other medium into a second flask and after 1 to 2 days form a monolayer.

If a monolayer of cells growing in a T-75 flask with 15 ml of medium reach confluence, they contact inhibit (stop growing) and begin to differentiate, and the culture dies, or passages very poorly.

However, the cells processed in accordance with the invention are not trypsinized to passage and do not contact inhibit. If the monolayer of the dermally derived keratinocytes, which attached within the 15 minute period, is fed about 3× the medium volume, that is 45 ml instead of 15 ml, the cells form a complete monolayer after 7-10 days and cells begin to grow up from the monolayer and "pop off." By "pop-off" is meant that as the cell divides to form 2 cells and since there is no available surface, the cells lift off the monolayer and up into suspension, in the medium overlaying the monolayer.

The cells that grow up and "pop off" the monolayer can be plated and form secondary cultures. Any method of separating cells from the "pop off" cell suspension known to those of ordinary skill can be used, as some examples only, such as Ficoll separation, FAS separation, and size distribution systems.

Figure 11A:
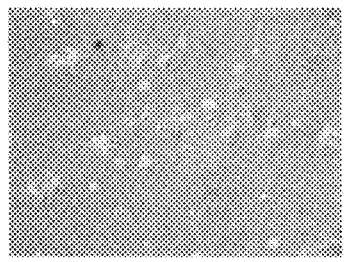
FIGS. 11a and b are photographs showing cells plating out from cell suspension derived from a primary monolayer.
Figure 11B:
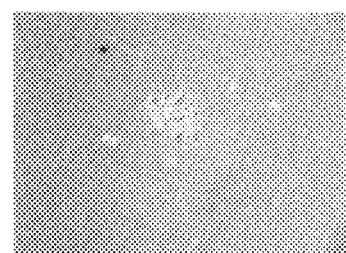
Figure 12:
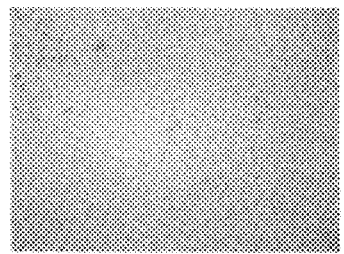
FIG. 12 shows colony growth after approximately one week.
Figure 13:
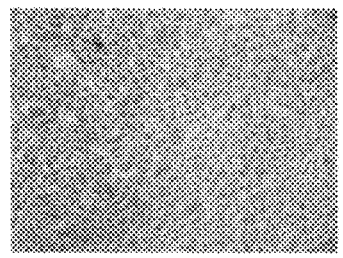
FIG. 13 is a photograph of a complete monolayer cell culture generated from cell colonies similar to that seen in FIG. 12 (primary cell suspension showing SM, MD, and LG cells).

When the floating cell suspension is transferred into another growth flask, for example, in spent or conditioned medium, the cells attach and grow. See for example, FIGS. 11a and b, showing cells plating out from cell suspension derived from a primary monolayer, and FIG. 12, showing colony growth after approximately one week. FIG. 11 shows small clear cell, sometimes forming form 4-5 cell colonies.

The cells grow as small cell colonies, initially 3-4 cells in number, to form 100-200, then 500 plus cell colonies that eventually coalesce to form a complete monolayer. (FIG. 12). After approximately one week of growth, one sees areas of colony growth, which eventually coalesce to form a monolayer of very small moderately growing cells. In FIG. 12 at the upper left, one sees the translation cells which will divide several times and senesce. In the right half are seen the very small moderately growing cells which have great colony forming ability. This culture arose from the cell suspension removed from a primary monolayer culture. The colonies coalesce to form complete monolayers that also produce floating cells in suspension. These cells can then be plated into flasks to form cultures that originated from the first cell suspension to form a tertiary culture.

Figure 14:
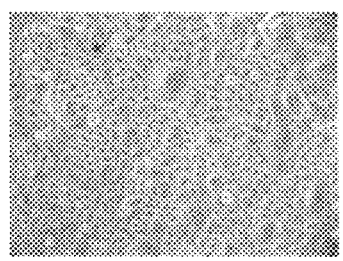
FIG. 14 is a photograph that shows a monolayer that grew from a secondary cell suspension.
Figure 15:
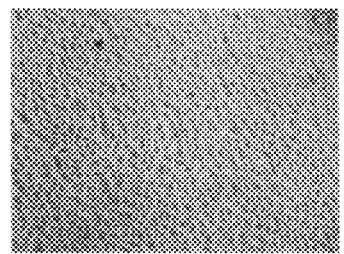
FIG. 15 is also a photograph showing a secondary cell suspension culture.
Figure 16:
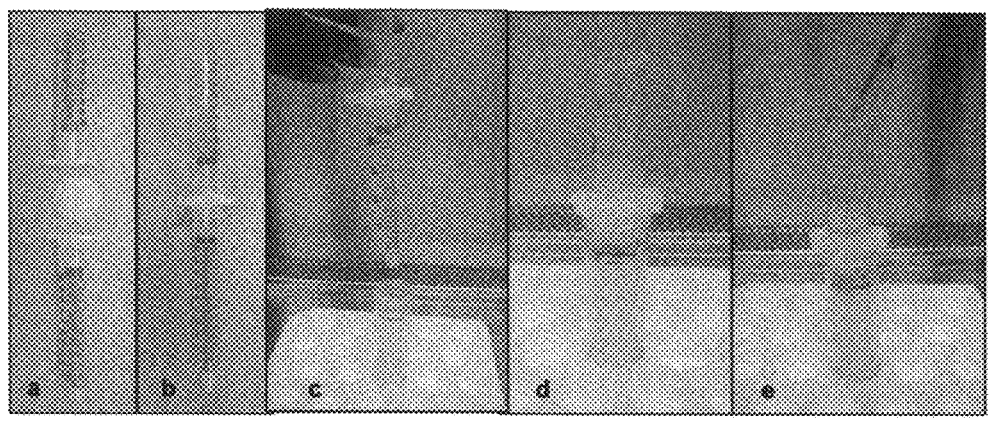
FIGS. 16A-E are photographs showing a series of steps in a cell filtration process in accordance with the invention.

Secondary cultures also have cells grow upward and "pop off". When these cells are plated into growth flasks, they again form small colonies, which grown, and then coalesce. (FIG. 13; this complete monolayer culture produced secondary cell suspensions.) Primary monolayers continue to form secondary cultures at each medium change, and the secondary cultures can then form tertiary cultures by plating the cells that "pop off" the secondary monolayers. Thus, at least "generations" of cultures may be propagated: primary culture, to suspension A1 to form monolayer A1 and yield suspension A2 which forms monolayer A2, which yields suspension A3 which forms culture A3. See FIG. 14, showing a culture arising from a secondary culture suspension. Notice that the cells have embedded highly differentiated cells surround by small moderately growing cells. Some intermediate sized cells are also seen. Also see FIG. 15, a secondary cell suspension culture; notice small uniform cell size. Thus, from the primary culture, suspension A, B, C, and D can be generated, at each cell feeding, and each of these can then create other cultures.

The cells that are generated from this techniques are small (12-15 microns), with compact nuclei, and with a rounded appearance. These cells fit the definition of an adult stem cell. These cells grow moderately fast. They double at one half to one third the rate of "normal keratinocyte cultures". These cultures, if treated with serum, calcium or fatty acids, will transform into the transitional cell cultures, which can be used to form in vitro grown skin for wound healing devices. Any epithelial type cell, whether from the eye, bladder, oral mucosa, epidermis, or other source, can be grown using our s procedure.

In accordance with the invention, any cell surface adhesion molecular surface for cell attachment can be used. Similarly, any specialized growth vessels, such as roller bottles, micro-carrier cell growth systems and suspension growth systems, or grooved surface vessels, can be used. Also, any growth system for automatically feeding the cultures can be used, i.e., rocker culture systems and the like. Finally, any combination of meshing filtration of cell suspensions with mesh of varying sizes can be used.

In additional embodiments, without limitation, the invention comprises other alternative approaches to using FACS as a primary cell sorting method. As one example only, embodiments of the invention comprise a serial filtration system that permits isolation of cells smaller than 11 microns, which in skin and mucosa is thought to contain a progenitor/stem cell population.

FIGS. 16A-E are photographs showing a series of steps in a cell filtration process in accordance with the invention. In the depicted embodiment, the serial cell filtration unit is comprised of the three components, an integrated combination of one sheet of nylon net filter, 25 mm disc, hydrophilic, 20 or 11 µm (Millipore) and two disposable syringes (20 mL or 10 mL). The tip of the syringe is cut off. Two syringes and the nylon net filter (20 or 11 µm) are integrated by bonding the wing of two syringes together with insertion of the nylon net filter between them (FIGS. 16A, B). The unit is autoclavable. The unit is placed passively into a 50 cc sterile conical tube (FIGS. 16C, D). A cell suspension is gently poured into the unit (FIG. 16E). The cell suspension goes through the inserted nylon net filter passively via gravity.

In this exemplary embodiment, human epidermal cells are obtained from surgical specimens of breast-reduction. Excess blood and adipose tissue underlying the skin sample are mechanically removed as much as possible in PBS. A piece of skin sample is incubated in penicillin/streptomycin solution in PBS for 3-4 hours. The skin is cut into 4 mm wide strips with a sterile scalpel, and soaked in 0.125% Trypsin solution in PBS overnight at room temperature. To neutralize trypsin, the tissue sample is transferred into a defined keratinocyte culture medium, EpiLife, supplemented with 2% fetal bovine serum (FBS). The cornified layer is gently peeled off from the tissue sample, and then the basal layer cells are scraped off into the culture medium from the dermis with a scalpel. To dissociate cells, cell suspension is vigorously pipetted. Large cell debris (including cornified layer) and clumped cells are filtered out by using 240 µm mesh, and the cell suspension is centrifuged at 24° C., 600 rpm for 5 minutes. The supernatant is aspirated and the cell pellet is resuspended with the EpiLife culture medium containing 2% FBS. This procedure is repeated one more time. The number of viable cell count harvested is performed by trypan blue staining under a hematocytometer. The final concentration of cell suspension prepared is about $6-10 \times 10^5$ cells/mL.

Figure 17:
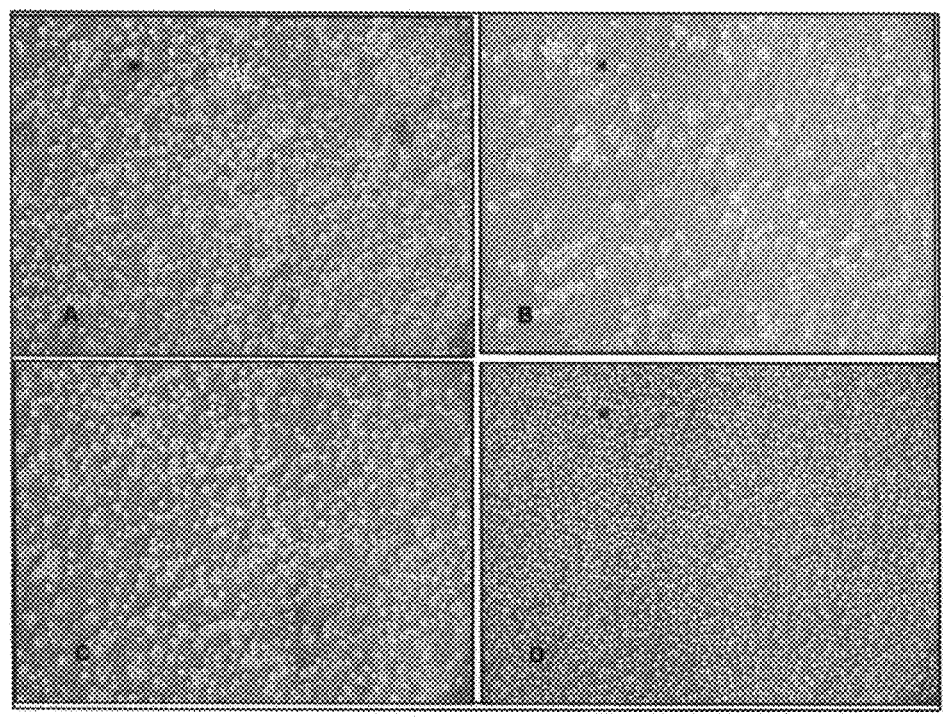
FIGS. 17A-D are photographs showing cells that have been filtered through a different sizes of nylon meshes: (A) non-filtered skin keratinocytes; (B) skin keratinocytes trapped by a 20 micron nylon filter; (C) skin keratinocytes trapped by a 11 micron nylon filter; and (D) final cell suspension of skin keratinocytes that have passed through the 11 micron nylon filter.

The wing of cell filtration device is placed onto the opening of 50 mL conical tube (FIGS. 16C, D). The cell suspension is gently poured into the open end of the device with 20 µm filter first (FIG. 16E). The cell suspension itself will slowly go through the nylon net filter and drop into the tube by gravitation. The procedure may be repeated with a 20 µm filter to collect smaller cells and remove larger cells and cluster of cells as many as possible. Finally, the 20 µm nylon net-filtered cell suspension is passed through the 11 µm nylon net once. Semi-purified small cell size population is in the final cell suspension. See FIG. 17, showing cells that have been filtered through a variety of size of nylon meshes as follows: (A) non-filtered skin keratinocytes; (B) skin keratinocytes trapped by a 20 micron nylon filter. (C) skin keratinocytes trapped by a 11 micron nylon filter; and (D) final cell suspension of skin keratinocytes that have passed through the 11 micron nylon filter. Note the uniform small size of these cells. In an alternate procedure, the mesh can be formed into a funnel, sterilized using conventional technology, and placed into a sterile conical tube. The cell suspension can be filtered using gravity Each of the references identified herein is hereby incorporated by reference as though fully set forth herein.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

REFERENCES

Alonso, L. and Fuchs, E. (2003) Stem cells of the skin epithelium. *Proc. Natl. Acad. Sci. USA* 100, 11830-11835.

Amit, M., Shariki, C., Margulets, V., Itskovitz-Eldor, J. (2004) Feeder layer- and serum-free culture of human embryonic stem cells. *Biol. Reprod.* 70, 837-845.

Barrandon, Y., and Green, H. (1985) Cell size as a determinant of the clone-forming ability of human keratinocytes *Proc. Natl. Acad. Sci. USA* 82, 5390-5394.

Barrandon, Y., and Green, H. (1987) Three clonal types of keratinocytes with different capacities for multiplication. *Proc. Natl. Acad. Sci. USA* 84, 2302-2306.

Bianco, P., and Robey, P. G. (2001) Stem cells in tissue engineering. *Nature* 414, 118-121.

Cao, T., Tasi, S. Y., O'Malley, B. W., Wang, X. J., Roop, D. R. (2002) The epidermis as a bioreactor: topically regulated cutaneous delivery into the circulation. *Hum. Gene Ther.* 13, 1075-1080.

Chen, M., Kasahara, N., Keene, D. R., Chan, L., Hoeffler, W. K., Finlay, D., Barcova, M., Cannon, P. M., Mazurek, C., Woodley, D. T. (2002) Restoration of type VII collagen expression and function in dystrophic epidermolysis bullosa. *Nat. Genet.* 32, 670-675.

Cutright, D. C. and Bauer, H. (1967) Cell renewal in the oral mucosa and skin of the rat: I. turnover time. *Oral Surg. Oral Med. Oral Pathol.* 23, 249-259.

Dunnwald, M., Tomanek-Chalkley, A., Alexandrunas, D., Fishbaugh, J., Bickenbach, J. R. (2001) Isolating a pure population of epidermal stem cells for use in tissue engineering. *Exp. Dermatol.* 10, 45-54.

Fuchs, E. and Raghavan, S. (2002) Getting under the skin of epidermal morphogenesis. *Nature Rev. Genetics* 3, 199-209.

Gibbs, S. and Ponec, M. (2000) Intrinsic regulation of differentiation markers in human epidermis, hard palate and buccal mucosa. *Arch. Oral Biol.* 45, 149-158.

Greenhalgh, D. A., Rothnagel, J. A., Roop, D. R. (1994) Epidermis: an attractive target tissue for gene therapy. *J. Invest. Dermatol.* 103, 63S-69S.

Hata, K., Kagami, H., Ueda, M., Torii, S., Matsuyama, M. (1995) The characteristics of cultured mucosal cell sheet as a material for grafting: Comparison with cultured epidermal sheet. *Ann. Plast. Surg.* 34, 530-538.

Hengge, U. R., Pfützner, W., Williams, M., Goos, M., Vogel, J. C. (1998) Efficient expression of naked plasmid DNA in mucosal epithelium: prospective for the treatment of skin lesions. *J. Invest. Dermatol.* 111, 605-608.

Izumi, K., Song, J., Feinberg, S. E. (2004) Development of a tissue engineered human oral mucosa: from the bench to the bed side. *Cells Tissues Organs* 176,134-152.

Izumi, K., Feinberg, S. E., Iida, A., Yoshizawa, M. (2003) Intraoral grafting of an ex vivo produced oral mucosa equivalent: A preliminary report. *Int. J. Oral Maxillofac. Surg* 32, 188-197.

Izumi, K., Terashi, H., Marcelo, C. L., Feinberg, S. E. (2000) Development and characterization of a tissue-engineered human oral mucosa equivalent produced in a serum-free culture system. *J. Dent. Res.* 79, 798-805.

Janes, S. M., Lowell, S., Hutter, C. (2002) Epidermal stem cells. *J. Pathol.* 197, 479-491.

Jiang, W. A., Redfern, A., Bryce, R. P., Mansel, R. E. (2000) Peroxisome proliferator activated receptor-γ (PPAR-γ) mediates the action of gamma linolenic acid in breast cancer cells. *Prostaglandin Lleukotriene Essnt. Fatty Acid* 62, 119-127.

Jones, J., Sugiyama, M., Watt, F. M., Speight, P. M. (1993) Integrin expression in normal, hyperplastic, dysplastic, and malignant oral epithelium. *J. Pathol* 169, 235-243.

Jones, P. H. and Watt, F. M. (1993) Separation of human epidermal stem cells from transit amplifying cells on the basis of differences in integrin function and expression. *Cell* 73, 713-724.

Kang, M. K., Bibb, C., Baluda, M. A., Rey, O., Park, N.-H. (2000) In vitro replication and differentiation of normal human oral keratinocytes. *Exp. Cell Res.* 258, 288-297.

Kaur, P. and Li, A. (2000) Adhesive properties of human basal epidermal cells: An analysis of keratinocyte stem cells, transit amplifying cells, and postmitotic differentiating cells. *J. Invest. Dermatol.* 114, 413-420.

Kaur, P., Li, A., Redvers, R., Bertoncello, I. (2004) Keratinocyte stem cell assays: An evolving science. *J. Invest. Dermatol. Symp. Proc.* 9, 238-247.

Kawakami, S., Arai, G., Hayashi, T., Fujii, Y., Xia, G., Kageyama, Y., Kihara, K. (2002) PPARγ ligands suppress proliferation of human urothelial basal cells in vitro. *J. Cell. Physiol.* 191, 310-319.

Kim D, Cho H, Choi, H, Kwon S, Park K. 2004. Isolation of human epidermal stem cells by adherence and the reconstruction of skin equivalents. 2004 *Cell. Mol. Life Sci.* 61, 2774-2781

Kolodka, T. M., Garlick, J. A. and Taichman, L. B. (1998) Evidence for keratinocyte stem cells in vitro: Long term engraftment and persistence of transgene expression from retrovirus-transduced keratinocyte. *Proc. Natl. Acad. Sci. USA* 95, 4356-4361.

Koster, M. I. and Roop, D. R. (2004) The role of p63 in development and differentiation of the epidermis. *J. Dermatol. Sci.* 34, 3-9.

Lavker, R. M. and Sun, T.-T. (2000) Epidermal stem cells: Properties, markers, and location. *Proc. Natl. Acad. Sci. USA* 97, 13473-13475.

Li, A., Pouliot, N.J., Redvers, R., Kaur, P. (2004) Extensive tissue-regenerative capacity of neonatal human keratinocytes stem cells and their progeny. *J. Clin. Invest.* 113, 390-400.

Li, A., Simmons, P. J., Kaur, P. (1998) Identification and isolation of candidate human keratinocyte stem cells based on cell surface phenotype. *Proc. Natl. Acad. Sci. USA* 95, 3902-3907.

Louët, S. (2004) Reagent safety issues surface for cell/tissue therapies. *Nat. Biotech.* 22, 253-254.

Mao-Qiang, M., Fowler, A. J., Schmuth, M., Lau, P., Chang, S., Brown, B. E., Moser, A. H., Michalik, L., Desvergne, B., Wahli, W., Li, M., Metzger, D., Chambon, P. H., Elias, P. M., and Feingold, K. R. (2004) Peroxisome-proliferator-activated receptor (PPAR) gamma activation stimulates keratinocyte differentiation. *J Invest Dermatol* 123, 305-312.

Mössner, R., Schulz, U., Krüger, U., Middel, P., Schinner, S., Füzesi, L., Neumann, C., Reich, K. (2002) Agonists of peroxisome proliferators-activated receptor y inhibit cell growth in malignant melanoma. *J. Invest. Dermatol.* 119, 576-582.

Nguyen, B. P., Ryan, M. C., Gil, S. G., Carter, W. G. (2000) Deposition of laminin 5 in epidermal wounds regulates integrin signaling and adhesion. *Curr. Opin. Cell Biol.* 12, 554-562.

Niemann, C. and Watt, F. M. (2002) Designer skin: lineage commitment in postnatal epidermis. *Trends in Cell Biol.* 12, 185-192.

Nikitakis, N. G., Hebert, C., Lopes, M. A., Reynolds, M. A., Sauk, J. J. (2002) PPARγ-mediated antineoplastic effect of nsaid sulindac on human oral squamous carcinoma cells. *Int. J. Cancer* 98, 817-823.

Ortiz-Urda, S., Thyagarajan, B., Keene, D. R., Lin, Q., Fang, M., Calos, M. P., Khavari, P. A. (2002) Stable nonviral genetic correction of inherited human skin disease. *Nature Med.* 8, 1166-1170.

Parsa, R., Yang, A., McKeon, F., Green, H. (1999) Association of p63 with proliferative potential in normal and neoplastic human keratinocytes. *J. Invest. Dermatol.* 113, 1099-1105.

Park H, Kang H, Kim Chang, Kim Chun, Han E, Han K, Kim T, Gin Y Son Y. 2004 Application of physical force is essential to enrich for epidermal stem cells in primary human keratinocyte isolation. *Tissue Engineering*, 10 (3/4), 343-351.

Pellegrini, G., Dellambra, E., Golisano, O., Martinelli, E., Fantozzi, I., Bondanza, S., Ponzin, D., McKeon, F., De Luca, M. (2001) p63 identifies keratinocyte stem cells. *Proc. Natl. Acad. Sci. USA* 98, 3156-3161.

Pfützner, W., Hengge, U. R., Joari, M. A., Foster, R. A., Vogel, J. C. (1999) Selection of keratinocytes transduced with the multidrug resistance gene in an in vitro skin model presents a strategy for enhancing gene expression in vivo. *Hum. Gene Ther.* 10, 2811-2821.

Pfützner, W., Terunuma, A., Tock, C. L., Snead, E. K., Kolodka, T. M., Gottesman, M. M., Taichman, L., Vogel, J. C. (2002) Topical colchicines selection of keratinocytes transduced with the multidrug resistance gene (MDR1) can sustain and enhance transgene expression in vivo. *Proc. Natl. Acad. Sci. USA* 99, 13096-13101.

Potten, C. S. and Booth, C. (2002). Keratinocyte stem cells: a commentary. *J. Invest. Dermatol.* 119, 888-899.

Rollman, O., Jensen, U. B., Ostman, A., Bolund, L., Gustafasdottir, S. M., Jensen, T. G. (2003) Platelet derived growth factor (PDGF) responsive epidermis formed from human keratinocytes transduced with the PDGFβ receptor gene. *J. Invest. Dermatol.* 120, 742-749.

Seery, J. P. and Watt, F. M. (2000) Asymmetric stem-cell divisions define the architecture of human oesophageal epithelium. *Curr. Biol.* 10, 1447-1450.

Serrano, F., Rio, M. D., Larcher, F., Garcia, M., Muñoz, E. Escamez, M. J., Muñoz, M., Meana, A., Bernoad, A., Jorcano, J. L. (2003) A comparison of targeting performance of oncoretroviral versus lentiviral vectors on human keratinocytes. *Hum. Gene Ther.* 14, 1579-1585.

Shi, S—R., Cote, R. J. and Taylor, C. R. (1997) Antigen retrieval immunohistochemistry: Past, present, and future. *J. Histochem. Cytochem.* 45, 327-343.

Smart, J. D. (2004) Lectin-mediated drug delivery in the oral cavity. *Adv. Drug Delivery* 56, 481-489.

Thompson, P. J., Potten, C. S., Appleton, D. R. (2001) In vitro labeling studies and the measurement of epithelial cell proliferative activity in the human oral cavity. *Arch. Oral Biol.* 46, 1157-1164.

Tiberio, R., Marconi, A., Fila, C., Fumelli, C., Pignatti, M., Krajewski, S., Giannetti, A., Reed, J. C., Pincelli, C. (2002) Keratinocytes enriched for stem cells are protected from anoikis via an integrin signaling pathway in a Bcl-2 dependent manner. *FEBS lett.* 524, 139-144.

Van Rossum, M. M., Schalkwijk, J., van de Kerkhof, P. C. M., van Erp, P. E. J. (2002) Immunofluorescent surface labeling, flow sorting and culturing of putative epidermal stem cells derived from small skin punch biopsies. *J. Immunol. Methods* 267, 109-117.

Vogel, J. C. (1993) Keratinocyte gene therapy. *Arch. Dermatol.* 129, 1478-1483.

Wan, H., Stone, M. G., Simpson, C., Reynolds, L. E., Marshall, J. F., Hart, I. R., Hodivala-Dilke, K. M. Eady, R. A. J. (2003) Desmosomal proteins, including desmoglein 3, serve as novel negative markers for epidermal stem cell-containing population of keratinocytes. *J. Cell Sci.* 116, 4239-4248.

Weinstein, G. D., McCullough, J. L., Ross, P. (1984) Cell proliferation in normal epidermis. *J. Invest. Dermatol.* 82, 623-628.

Westergaard, M., Henningsen, J., Svendsen, M. L., Johansen, C., Jensen, U. B., SchrØder, H. D., Kratchmarova, I., Berge, R. K., Iversen, L., Bolund, L., Kragballe, K., Kristiansen, K. (2001) Modulation of keratinocyte gene expression and differentiation by PPAR-selective ligands and tetradecylthioacetic acid. *J. Invset. Dermatol.* 116, 702-712.

Winning, T. A. and Townsend, G. C. (2000) Oral mucosal embryology and histology. *Clinic. Dermatology* 18, 499-511.

Youn, S. W., Kim, D. S., Cho, H. J., Jeon, S. E., Bae, I. H., Yoon, H. J., Park, K. C. (2004) Cellular senescence induced loss of stem cell proportion in the skin in vitro. *J. Dermatol. Sci.* 35, 113-123.

What is claimed is:

1. A method of preparing a stem cell-enriched cell population, comprising the steps of:
    providing a biological material containing epidermis and dermis;
    dissociating dermis from epidermis by trypsinization and mechanical separation, in any order;
    collecting the epidermal cells from the trypsinized dermis;
    centrifuging and resuspending the cells in growth media with 2% serum to contain a concentration of about 20 million collected cells per 15 ml of growth media, wherein the growth media is devoid of bovine pituitary extract;
    incubating the cell suspension in a coated container, wherein the coated container is devoid of a xenogeneic feeder layer and bovine pituitary extract;
    removing the cell suspension containing unattached cells and adding serum-free, fatty acid-free media to the container containing attached cells in a ratio of media volume to standard container volume that is a multiple of the standard container volume;
    incubating the attached cells in the presence of excess media; and
    removing and resuspending cells which have grown and detached from the attached cells in the container.

2. The method of claim 1, wherein the container is comprised of a tissue culture coating.

3. The method of claim 1, further comprising the step of incubating the removed and resuspended cells to form a second generation of monolayer cultures.

4. A method of preparing a stem cell-enriched cell population, comprising the steps of:
    providing a biological material containing epidermis and dermis;
    dissociating dermis from epidermis by trypsinization and mechanical separation, in any order;
    collecting the epidermal cells from the trypsinized dermis;
    suspending the cells in growth media with serum; wherein the growth media is devoid of a xenogeneic feeder layer and bovine pituitary extract;
    further dissociating the cells from other debris by mechanical force;
    filtering the cell suspension through a filter of about 240 micron mesh;
    centrifuging the filtered cell suspension, aspirating the supernatant, and resuspending the cell pellet in growth media with serum to a concentration of about 600,000 cells per ml;
    pouring the cell suspension over a filtration device comprising sequential 20 micron and 11 micron filters; and
    collecting the suspension of cells passing through the 11 micron filter, wherein the filters in the filtration device separate the cells in the suspension size.

5. The method of claim 1, further comprising the step of further trypsinizing the dermis to remove epidermal cells after the step of dissociating dermis from epidermis by trypsinization and mechanical separation.

6. The method of claim 1 or claim 5, wherein the multiple of the container working volume is 3×.

7. A method of preparing a stem cell-enriched cell population comprising the steps of:
    providing a biological material containing epidermis and dermis;
    dissociating dermis from epidermis by trypsinization and mechanical separation, in any order;
    collecting the epidermal cells from the trypsinized dermis;
    centrifuging and resuspending the cells in growth media with 2% serum, wherein the growth media is devoid of bovine pituitary extract;
    incubating the cell suspension in a coated container for a time sufficient to obtain cells attached to a surface of the container, wherein the coated container is devoid of a xenogeneic feeder layer and bovine pituitary extract;
    removing the cell suspension containing any unattached cells and adding serum-free, fatty acid-free media to the container containing attached cells in a ratio of media volume to standard container volume that is a multiple of the standard container volume;
    incubating the attached cells in the presence of excess media for a time sufficient to form a complete monolayer of attached cells in the container; and
    removing and resuspending cells which have grown and detached from the attached cells in the container.

8. The method of claim 7, wherein the container is comprised of a tissue culture coating.

9. The method of claim 7, further comprising the step of incubating the removed and resuspended cells to form a second generation of monolayer cultures.

10. The method of claim 1 or claim 7, wherein the container is comprised of a T-25 flask or a T-75 flask.

11. The method of claim 10, wherein the multiple of the container working volume is at least 3×.

* * * * *